United States Patent
Baker, Jr. et al.

(10) Patent No.: US 6,471,968 B1
(45) Date of Patent: Oct. 29, 2002

(54) MULTIFUNCTIONAL NANODEVICE PLATFORM

(75) Inventors: James R. Baker, Jr., Ann Arbor, MI (US); Donald A. Tomalia, Ann Arbor, MI (US)

(73) Assignee: Regents of the University of Michigan, Ann Arbor, MI (US)

(*) Notice: Subject to any disclaimer, the term of this patent is extended or adjusted under 35 U.S.C. 154(b) by 0 days.

(21) Appl. No.: 09/570,198

(22) Filed: May 12, 2000

(51) Int. Cl.[7] .................. C07H 21/04; A61K 48/00; A61K 43/00
(52) U.S. Cl. .............. 424/280.1; 424/1.11; 424/277.1; 424/94.1; 424/130.1; 514/44; 536/23.1; 536/24.1; 536/24.5
(58) Field of Search .................. 536/23.1, 24.1, 536/24.5; 514/44; 530/300, 351, 397, 399, 402; 424/130.1, 184.1, 94.1, 1.11, 277.1, 283.1, 280.1

(56) References Cited

U.S. PATENT DOCUMENTS

| | | |
|---|---|---|
| 4,507,466 A | 3/1985 | Tomalia et al. |
| 4,558,120 A | 12/1985 | Tomalia et al. |
| 4,568,737 A | 2/1986 | Tomalia et al. |
| 4,587,329 A | 5/1986 | Tomalia et al. |
| 4,631,337 A | 12/1986 | Tomalia et al. |
| 4,694,064 A | 9/1987 | Tomalia et al. |
| 4,708,930 A | 11/1987 | Kortright et al. |
| 4,713,975 A | 12/1987 | Tomalia et al. |
| 4,737,550 A | 4/1988 | Tomalia |
| 4,743,543 A | 5/1988 | Kortright |
| 4,857,599 A | 8/1989 | Tomalia et al. |
| 4,871,779 A | 10/1989 | Killat et al. |
| 4,892,935 A | 1/1990 | Yoshida et al. |
| 4,914,021 A | 4/1990 | Toth et al. |
| 4,918,164 A | 4/1990 | Hellstrom et al. |
| 4,921,789 A | 5/1990 | Salem et al. |
| 4,921,790 A | 5/1990 | O'Brien |
| 4,939,240 A | 7/1990 | Chu et al. |
| 4,946,778 A | 8/1990 | Ladner et al. |
| 4,963,484 A | 10/1990 | Kufe |
| 5,053,489 A | 10/1991 | Kufe |
| 5,110,911 A | 5/1992 | Samuel et al. |
| 5,270,163 A | 12/1993 | Gold et al. |
| 5,338,532 A | 8/1994 | Tomalia et al. |
| 5,354,308 A | 10/1994 | Simon et al. |
| 5,387,617 A | 2/1995 | Hedstrand et al. |
| 5,393,795 A | 2/1995 | Hedstrand et al. |
| 5,393,797 A | 2/1995 | Hedstrand et al. |
| 5,475,096 A | 12/1995 | Gold et al. |
| 5,512,443 A | 4/1996 | Schlom et al. |
| 5,527,524 A | 6/1996 | Tomalia et al. |
| 5,545,530 A | 8/1996 | Satomura et al. |
| 5,560,929 A | 10/1996 | Hedstrand et al. |
| 5,631,329 A | 5/1997 | Yin et al. |
| 5,661,025 A | 8/1997 | Szoka et al. |
| 5,674,192 A | 10/1997 | Sahatjian et al. |
| 5,693,014 A | 12/1997 | Abele et al. |
| 5,693,763 A | 12/1997 | Codington et al. |
| 5,714,166 A | 2/1998 | Tomalia et al. |
| 5,733,303 A | 3/1998 | Israel et al. |
| 5,755,722 A | 5/1998 | Barry et al. |
| 5,773,527 A | 6/1998 | Tomalia et al. |
| 5,792,105 A | 8/1998 | Lin et al. |
| 5,795,582 A | 8/1998 | Wright |
| 5,800,391 A | 9/1998 | Kontos |
| 5,800,508 A | 9/1998 | Goicoechea et al. |
| 5,800,519 A | 9/1998 | Sandock |
| 5,808,005 A | 9/1998 | Codington et al. |
| 5,843,089 A | 12/1998 | Sahatjian et al. |
| 5,851,228 A | 12/1998 | Pinheiro |
| 5,855,866 A | 1/1999 | Thorpe et al. |
| 5,857,998 A | 1/1999 | Barry |
| 5,861,319 A | 1/1999 | Lin et al. |
| 5,866,561 A | 2/1999 | Ungs |
| 5,868,719 A | 2/1999 | Tsukernik |
| 5,876,445 A | 3/1999 | Andersen et al. |
| 5,892,019 A | 4/1999 | Schlom et al. |
| 5,892,020 A | 4/1999 | Mezes et al. |
| 5,898,005 A | 4/1999 | Singh et al. |
| 5,902,863 A | 5/1999 | Dvornic et al. |
| 5,908,413 A | 6/1999 | Lange et al. |
| 5,913,894 A | 6/1999 | Schmitt |
| 5,933,145 A | 8/1999 | Meek |
| 5,935,114 A | 8/1999 | Jang et al. |

FOREIGN PATENT DOCUMENTS

| | | |
|---|---|---|
| WO | WO9002545 | 3/1990 |
| WO | WO 97/38134 | 10/1997 |
| WO | WO 98/33941 | 8/1998 |
| WO | WO 99/02651 | 1/1999 |
| WO | WO 99/07724 | 2/1999 |

OTHER PUBLICATIONS

Friedman, Cancer 70:1810 [1992].
Kerr et al., Cancer 73:2013 [1994].
Cohen and Tohoku, Exp. Med., 168:351 [1992].
Fujiwara et al., J. Natl. Cancer Inst., 86:458 [1994].
Tomalia, Advanced Materials 6:529 [1994].
Tomalia, Angew, Chem. Int. Ed. Engl., 29:138 [1990].
Tomalia et al., Chem. Int. Ed. Engl., 29:5305 [1990].
Yin et al., J. Am. Chem. Soc., 120:2678 [1998].
Roberts et al., J. Biomed. Mat. Res. 30:53 [1996].
Bourne et al., J. Magn. Reson. Imag., 6:305 [1996].

(List continued on next page.)

*Primary Examiner*—Sean McGarry
*Assistant Examiner*—Karen A. Lacourciere
(74) *Attorney, Agent, or Firm*—Medlen & Carroll, LLP

(57) ABSTRACT

The present invention relates to novel therapeutic and diagnostic arrays. More particularly, the present invention is directed to dendrimer based multifunctional compositions and systems for use in disease diagnosis and therapy (e.g., cancer diagnosis and therapy). The compositions and systems generally comprise two or more separate components for targeting, imaging, sensing, and/or triggering release of a therapeutic or diagnostic material and monitoring the response to therapy of a cell or tissue (e.g., a tumor).

34 Claims, 9 Drawing Sheets

OTHER PUBLICATIONS

Singh et al., Clin. Chem., 40:1845 [1994].
Wu et al., Bioorg. Med. Chem. Lett., 4:449 [1994].
Wiener et al., Magn. Reson. Med. 31:1 [1994].
Barth et al., Bioconjugate Chem. 5:58 [1994].
Duncan and Malik, Control Rel. Bioact. Mater. 23:105 [1996].
Baker et al., Anal. Chem. 69:990 [1997].
Urdea and Hom, Science 261:534 [1993].
Lanni et al., Proc. Natl. Acad. Sci., 94:9679 [1997].
Tortora et al., Cancer Research 57:5107 [1997].
Zaffaroni et al., Brit. J. Cancer 77:1378 [1998].
Yu et al., Molecular Cell. 2:581 [1998].
Gibb, Gynecologic Oncology 65:13 [1997].
Akutsu et al., Eur. J. Cancer 31A:2341 [1995].
Pasani et al., Inorg. Chim. Acta 80:99 [1983].
Ottl et al., Bioconjugate Chem., 9:143 [1998].
Abel et al., Eur. J. Cancer 9:4 [1973].
Pillai, V.N.R. Synthesis: 1–26 [1980].
Esfand et al., Pharm. Sci., 2:157 [1996].
Vasey et al., Clin. Cancer Res., 5:83 [1999].
Capala et al., Bioconjugate Chem., 7:7 [1996].
Selman, et al., Photochem. Photobio., 57:681–85 [1993].
Brasseur et al., Photochem. Photobiol., 47:705–11 [1988].
Firey and Rodgers, Photochem. Photobiol., 45:535–38 [1987].
Sessler et al., Proc. SPIE, 1426:318–29 [1991].
Chang et al., Proc. SPIE, 1203:281–86 [1990].
Cincotta et al., SPIE Proc., 1203:202–10 [1990].
Pandey et al., Photochem. Photobiol., 53:65–72 [1991].
Botchway et al., Photochem. Photobiol. 67(7):635–40 [1998].
Liao et al., PNAS 91:2659 [1994].
Murphy et al., Neuropharm. 33:1375–85 [1994].
Bourassa et al., JACS 119:2853–60 [1997].
De Leo and Ford, JACS 121:1980–81 [1999].
Chan and Nie, Science 281:2016 [1998].
Sooklal, Adv. Mater., 10:1083 [1998].
Balogh et al., Proc. of ACS PMSE 77:118 [1997].
Balogh and Tomalia, J. Am. Che. Soc., 120:7355 [1998].
Wiener et al., Mag. Reson. Med. 31:1 [1994].
Wong et al., Ivest. Rad. 31:26 [1996].
Farkas et al., SPEI 2678:200 [1997].
Lester et al., Cell Mol. Biol. 44:29 [1998].
Shortreed et al., J. Phys. Chem. 101:6318 [1997].
Talanian et al., J. Biol. Chem., 272:9677 [1997].
Abrams et al., Development 117:29 [1993].
Hockenbery et al., Cell 75:241 [1993].
Wiener et al., Invest. Radiol., 32:748 [1997].
Capale et al., Bioconjugate Chem., 7:7 [1996].
Penault–Llorca et al., Int. J. Cancer 61:170 [1995].
Press et al., Oncogene 5:953 [1990].
Pegrarn et al., Proc. Am. Soc. Clin. Oncol., 14:106 [1995].
Park et al., Cancer Lett., 118:153 [1997].
Kirpotin et al., Biochem., 36:66 [1997].
Kjeldsen et al., Cancer Res. 48:2214–2220 [1988].
Springer et al., Carbohydr. Res. 178:271–292 [1988].
Tjandra et al., Br. J. Surg. 75:811–817 [1988].
Ishida et al., Tumor Biol. 10:12–22 [1989].
Lan et al., Cancer Res. 45:305–310 [1985].
Hanisch et al., Carbohydr. Res. 178:29–47 [1988].
Hinoda et al., (1988) Cancer J. 42:653–658 [1988].
Köhler and Milstein, Nature 256:495–497 [1975].
Kozbor et al. Immunol. Today 4:72 [1983].
Cole et al., in Monoclonal Antibodies and Cancer Therapy, Alan R. Liss, Inc., pp. 77–96 [1985].
Cote et al., Proc. Natl. Acad. Sci. U.S.A.80:2026–2030 [1983].
Huse et al., Science 246:1275–1281 [1989].
Duncan et al., Polymer Preprints 39:180 [1998].
Sharon and Lis, Science 246:227 [1989].
Monsigny et al., Biochemie 70:1633 [1988].
Page and Roy, Bioconjugate Chem., 8:714 [1997].
Cortese et al., Curr. Opin. Biotechol., 6:73 [1995].
Goodwin and Meares, Cancer (suppl.) 80:2675 [1997].
Wilbur et al., Bioconjugate Chem.,9:813 [1998].
Barth et al., Cancer Investigation 14:534 [1996].
Duncan and Sat, Ann. Oncol., 9:39 [1998].
Malik et al., Proc. Int'l. Symp. Control. Rel. Bioact. Mater., 24:107 [1997].
Wies et al., Nature 333: 426 [1988].
White et al., Cell 56: 725 [1989].
Wyrick et al., Infect. Imm. 57:2378 [1989].
Adlish et al., Virology 176: 337 [1990].
Krah, Virology 172:386 [1989].
Khatzman et al., Nature 312:763 [1985].
Sacerdote et al., J. of Neuroscience Research 18: 102 [1987].
Ruff et al., FEBS Letters 211: 17 [1987].
Epstein et al., Nature 318:663 [1985].
Lentz et al., Science 215: 182 [1982].
Carel et al., J. Biol. Chem. 265: 12293 [1990].
Co et al., Proc. Natl. Acad. Sci. 82: 1494 [1985].
Marlin et al., Nature 344: 70 [1990].
Shephey et al., Proc. Natl. Acad. Sci. 85: 7743 [1988].
Mendelsohn et al., Cell 56: 855 [1989].
Kaner et al., Science 248: 1410 [1990].
Tuerk et al., Gene 137(1):33–9 [1993].
Binkley et al., Nuc. Acids Res. 23(16):3198–205 [1995].
Jellinek et al., Biochem. 83(34):10450–6 [1994].
Uppuluri et al., PMSE 80:55 [1999].
Mosmann, J. Immunol. Meth., 65:55 [1983].
Kuhlmann et al., Arch. Toxicol., 72:536 [1998].
Bielinska et al., Nucleic Acids Research 24:2176–2182 (1996).
Kukowska–Latallo et al., Proc.Natl. Acad. Sci. USA 93:4897–4902 (1996).
Bielinska et al., Biochimica et Biophysica Acta 1353:180–190 (1997).
Wagner, Journal of Controlled Release 53:155–158 (1998).
Brazeau et al., Pharm. Research 15:680–684 (1998).
Shchepinov et al., Nucleic Acids Research 25:4447–4454 (1997).
Haensler et al., Bioconjugate Chem. 4:373–379 (1993).
Orentas et al., Journal of Virological Methods 77:153–163 (1999).
Choi et al., Bioconjugate Chem. 10:62–65 (19999).
Ruponen et al., Biochimica et Biophysica Acta 1415:331–341 (1999).
Baker et al., Kluwer Academic Publishers, Manufactured in the Netherlands 61–690 (2001).

Option 1: Single Dendrimer Agent (70 Å in diameter)

All of the different components are carried on a single dendritic polymer, and must be individually conjugated to the therapeutic.

Option 2: Dendrimer Cluster Agent (approx. 200Å in diameter)

Breast Adenocarcinoma Therapeutic Device

Colon Adenocarcinoma Therapeutic Device

A

B

C

D

SEQUENCE LISTING

<160> NUMBER OF SEQ ID NOS: 1

<210> SEQ ID NO 1
<211> LENGTH: 7
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (1)..(1)
<223> OTHER INFORMATION: Xaa at this position is MCA-Tyr , a
    7-methoxycoumarin-4-yl-tyrosine
<221> NAME/KEY: SITE
<222> LOCATION: (7)..(7)
<223> OTHER INFORMATION: Xaa at this position is Lys-DNP-NH2 , a
    2,4-dinitrophenyl-lysine.

<400> SEQUENCE: 1

Xaa Glu Val Asp Gly Trp Xaa
1               5

MULTIFUNCTIONAL NANODEVICE PLATFORM

FIELD OF THE INVENTION

The present invention relates to novel therapeutic and diagnostic systems. More particularly, the present invention is directed to dendrimer based multifunctional compositions and systems for use in disease diagnosis and therapy (e.g. cancer diagnosis and therapy). The compositions and systems generally comprise two or more separate components for targeting, imaging, sensing, and/or triggering release of a therapeutic or diagnostic material and monitoring the response to therapy of a cell or tissue (e.g., a tumor).

BACKGROUND OF THE INVENTION

New initiatives in chemotherapeutics and radiopharmaceutics have improved the survival of patients with many forms of neoplasm. Several cancers now have five year survival rates greater than 80 percent. However, despite these successes, many problems still exist concerning cancer therapy. For example, many common neoplasms, such as colon cancer, respond poorly to available therapies.

For tumor types that are responsive to current methods, only a fraction of cancers respond well to the therapies. In addition, despite the improvements in therapy for many cancers, most currently used therapeutic agents have severe side effects. These side effects often limit the usefulness of chemotherapeutic agents and result in a significant portion of cancer patients without any therapeutic options. Other types of therapeutic initiatives, such as gene therapy or immunotherapy, may prove to be more specific and have fewer side effects than chemotherapy. However, while showing some progress in a few clinical trials, the practical use of these approaches remains somewhat limited at this time.

Despite the limited success of existing therapies, the understanding of the underlying biology of neoplastic cells has advanced. The cellular events involved in neoplastic transformation and altered cell growth are now identified and the multiple steps in carcinogenesis of several human tumors have been documented (See e.g., Isaacs, Cancer 70:1810 [1992]). Oncogenes that cause unregulated cell growth have been identified and characterized as to genetic origin and function. Specific pathways that regulate the cell replication cycle have been characterized in detail and the proteins involved in this regulation have been cloned and characterized. Also, molecules that mediate apoptosis and negatively regulate cell growth have been clarified in detail (Kerr et al., Cancer 73:2013 [1994]). It has now been demonstrated that manipulation of these cell regulatory pathways has been able to stop growth and induce apoptosis in neoplastic cells (See e.g., Cohen and Tohoku, Exp. Med., 168:351 [1992] and Fujiwara et al., J. Natl. Cancer Inst., 86:458 [1994]). The metabolic pathways that control cell growth and replication in neoplastic cells are important therapeutic targets.

Despite these impressive accomplishments, many obstacles still exist before these therapies can be used to treat cancer cells in vivo. For example, these therapies require the identification of specific pathophysiologic changes in an individual's particular tumor cells. This requires mechanical invasion (biopsy) of a tumor and diagnosis typically by in vitro cell culture and testing. The tumor phenotype then has to be analyzed before a therapy can be selected and implemented. Such steps are time consuming, complex, and expensive.

There is a need for treatment methods that are selective for tumor cells compared to normal cells. Current therapies are only relatively specific for tumor cells. Although tumor targeting addresses this selectivity issue, it is not adequate, as most tumors do not have unique antigens. Further, the therapy ideally should have several, different mechanisms of action that work in parallel to prevent the selection of resistant neoplasms, and should be releasable by the physician after verification of the location and type of tumor. Finally, the therapy ideally should allow the physician to identify residual or minimal disease before and immediately after treatment, and to monitor the response to therapy. This is crucial since a few remaining cells may result in re-growth, or worse, lead to a tumor that is resistant to therapy. Identifying residual disease at the end of therapy (i.e., rather than after tumor regrowth) would facilitate eradication of the few remaining tumor cells.

Thus, an ideal therapy should have the ability to target a tumor, image the extent of the tumor and identify the presence of the therapeutic agent in the tumor cells. It ideally allows the physician to determine why cells transformed to a neoplasm, to select therapeutic molecules based on the pathophysiologic abnormalities in the tumor cells, to activate the therapeutic agents only in abnormal cells, to document the response to the therapy, and to identify residual disease.

SUMMARY OF THE INVENTION

The present invention relates to novel therapeutic and diagnostic systems. More particularly, the present invention is directed to dendrimer based multifunctional compositions and systems for use in disease diagnosis and therapy (e.g., cancer diagnosis and therapy). The compositions and systems generally comprise two or more distinct components for targeting, imaging, sensing, and/or triggering release of a therapeutic or diagnostic material and monitoring the response to therapy of a cell or tissue (e.g., a tumor).

For example, the present invention provides a composition comprising a dendrimer complex, said dendrimer complex comprising first and second dendrimers, the first dendrimer comprising a first agent and the second dendrimer comprising a second agent, wherein the first agent is different than the second agent. In preferred embodiments, the first and said second agents are selected from the group consisting of therapeutic agents, biological monitoring agents, biological imaging agents, targeting agents, and agents capable of identifying a specific signature of cellular abnormality. In some embodiments, the first dendrimer is covalently linked to the second dendrimer. In certain embodiments, the dendrimer complex includes additional dendrimers. For example, in some embodiments, the complex comprises a third dendrimer (e.g., a third-dendrimer covalently linked to the first and second dendrimers). In yet other embodiments, the dendrimer complex comprises fourth, fifth, or additional dendrimers. Each of the dendrimers may comprise an agent.

In some embodiments, the present invention provides a composition comprising: a first dendrimer comprising a first agent; and a second dendrimer comprising a second agent, wherein the first and second dendrimers are complexed (e.g., covalently attached) with at least one dendrimer (e.g., to each other, to a common third dendrimer, or each individually to a third and fourth dendrimers respectively), and wherein the first agent is different than the second agent, and wherein the first and the second agents are selected from the group consisting of therapeutic agents, biological monitoring agents (i.e., agents capable of monitoring biological materials or events), biological imaging agents (i.e., agents capable of imaging biological materials or events), targeting agents (i.e., agents capable of targeting a biological material—i.e., specifically interacting with the biological material), and agents capable of identifying a specific signature of cellular identity (i.e., capable of identifying a characteristic of a cell that helps differentiate the cell from other cell types—e.g., a cellular proteins specific for a particular cellular abnormality). The present invention is not limited by the nature of the dendrimers. Dendrimers suitable for use with the present invention include, but are not limited to, polyamidoamine (PAMAM), polypropylamine (POPAM), polyethylenimine, iptycene, aliphatic poly (ether), and/or aromatic polyether dendrimers. Each dendrimer of the dendrimer complex may be of similar or different chemical nature than the other dendrimers (e.g., the first dendrimer may comprises a PAMAM dendrimer, while the second dendrimer may comprises a POPAM dendrimer). In some embodiments, the first or second dendrimer may further comprises an additional agent.

In some embodiments of the present invention, the dendrimer complex may further comprises one or more additional dendrimers. For example, the composition may further comprises a third dendrimer; wherein the third-dendrimer is complexed with at least one other dendrimer. In some embodiments, a third agent is complexed with the third dendrimer. In some embodiments, the first and second dendrimers are each complexed to a third dendrimer. In preferred embodiments, the first and second dendrimers comprise PAMAM dendrimers and the third dendrimer comprises a POPAM dendrimer. In certain embodiments, the present invention further comprises fourth and/or fifth dendrimers comprising agents (e.g., third and fourth agents), wherein the fourth and/or fifth dendrimer is also complexed (e.g., covalently attached) to the third dendrimer. The present invention is not limited by the number of dendrimers complexed to one another.

In some embodiments of the present invention, the first agent is a therapeutic agent and the second agent is a biological monitoring agent. In preferred embodiments, the therapeutic agent includes, but is not limited to, a chemotherapeutic agent, an anti-oncogenic agent, an anti-vascularizing agent, a anti-microbial or anti-pathogenic agent, and an expression construct comprising a nucleic acid encoding a therapeutic protein. In some embodiments, the therapeutic agent is protected with a protecting group selected from photo-labile, radio-labile, and enzyme-labile protecting groups. In preferred embodiments, the chemotherapeutic agents include, but are not limited to, platinum complex, verapamil, podophyllotoxin, carboplatin, procarbazine, mechlorethamine, cyclophosphamide, camptothecin, ifosfamide, melphalan, chlorambucil, bisulfan, nitrosurea, adriamycin, dactinomycin, daunorubicin, doxorubicin, bleomycin, plicomycin, mitomycin, etoposide, tamoxifen, taxol, transplatinum, 5-fluorouracil, vincristin, vinblastin, and methotrexate. In some embodiments, the anti-oncogenic agent comprises an antisense nucleic acid. In certain embodiments, the antisense nucleic acid comprises a sequence complementary to an RNA of an oncogene. In preferred embodiments, the oncogene includes, but is not limited to, abl, Bcl-2, Bcl-$x_1$, erb, fms, gsp, hst, jun, myc, neu, raf; ras, ret, src, or trk. In some embodiments, the nucleic acid encoding a therapeutic protein encodes a factor including, but not limited to, a tumor suppressor, cytokine, receptor, inducer of apoptosis, or differentiating agent. In preferred embodiments, the tumor suppressor includes, but is not limited to, BRCA1, BRCA2, C-CAM, p16, p21, p53, p73, Rb, and p27. In preferred embodiments, the cytokine includes, but is not limited to, GMCSF, IL-1, IL-2, IL-3, IL-4, IL-5, IL-6, IL-7, IL-8, IL-9, IL-10, IL-11, IL-12, IL-13, IL-14, IL-15, β-interferon, γ-interferon, and TNF. In preferred embodiments, the receptor includes, but is not limited to, CFTR, EGFR, estrogen receptor, IL-2 receptor, and VEGFR. In preferred embodiments, the inducer of apoptosis includes, but is not limited to, AdE1B, Bad, Bak, Bax, Bid, Bik, Bim, Harakid, and ICE-CED3 protease. In some embodiments, the therapeutic agent comprises a short-half life radioisotope.

In some embodiments of the present invention, the biological monitoring agent comprises an agent that measures an effect of a therapeutic agent (e.g., directly or indirectly measures a cellular factor or reaction induced by a therapeutic agent), however, the present invention is not limited by the nature of the biological monitoring agent. In some embodiments, the monitoring agent is capable of measuring the amount of or detecting apoptosis caused by the therapeutic agent.

In some embodiments of the present invention, the imaging agent comprises a radioactive label including, but not limited to, $^{14}C$, $^{36}Cl$, $^{57}Co$, $^{58}Co$, $^{51}Cr$, $^{125}I$, $^{131}I$, $^{111}In$, $^{152}Eu$, $^{59}Fe$, $^{67}Ga$, $^{32}P$, $^{186}Re$, $^{35}S$, $^{75}Se$, Tc-99m, and $^{169}Yb$, however, the present invention is not limited by the nature of the imaging agent.

In some embodiments of the present invention, the targeting agent includes, but is not limited to an antibody, receptor ligand, hormone, vitamin, and antigen, however, the present invention is not limited by the nature of the targeting agent. In some embodiments, the antibody is specific for a disease specific antigen. In some preferred embodiments, the disease specific antigen comprises a tumor specific antigen. In some embodiments, the receptor ligand includes, but is not limited to, a ligand for CFTR, EGFR, estrogen receptor, FGR2, folate receptor, IL-2 receptor, glycoprotein, and VEGFR.

The present invention also provides methods for treating a cell with a dendrimer complex comprising: providing a cell and a composition comprising a dendrimer complex, and exposing the cell to the dendrimer complex. In some embodiments, the dendrimer complex comprises a first dendrimer comprising a first agent, and a second dendrimer comprising a second agent, wherein the first and second dendrimers are complexed with at least one dendrimer, and wherein the first agent is different than the second agent, and wherein the first and the second agents are selected from the group consisting of therapeutic agents, biological monitoring agents, biological imaging agents, targeting agents, and agents capable of identifying a specific signature of cellular abnormality; and exposing the cell to the composition. The present invention is not limited by the nature of the cell type or the exposing step. For example, cells of the present invention include, but are not limited to, cell residing in vitro (e.g., cell culture cells) and cells residing in vivo (e.g., cells of a human or animal subject or pathogenic cells). In preferred embodiments, where the cell resides in a subject (e.g., a human or animal subject), the subject has a disease (e.g., the cell is a disease cell such as a tumor cell). In some embodiments, the disease includes, but is not limited to, cancer, cardiovascular disease, inflammatory disease, and prion-type disease (i.e., diseases associated with or caused by a prion).

In some embodiments of the present invention, the therapeutic agent is in inactive form and is rendered active following administration of the composition to the subject. For example, the agent, upon exposure to light or a change in pH (e.g., due to exposure to a particular intracellular environment) is altered to assume its active form. In these embodiments, the agent may be attached to a protective linker (e.g., photo-cleavable, enzyme-cleavable, pH-cleavable) to make it inactive and become active upon exposure to the appropriate activating agent (e.g., UV light, a cleavage enzyme, or a change in pH).

In some embodiments of the present invention, the subject has a tumor or is suspected of having cancer. In certain embodiments the cancer includes, but is not limited to, lung, breast, melanoma, colon, renal, testicular, ovarian, lung, prostate, hepatic, germ cancer, epithelial, prostate, head and neck, pancreatic cancer, glioblastoma, astrocytoma, oligodendroglioma, ependymomas, neurofibrosarcoma, meningia, liver, spleen, lymph node, small intestine, colon, stomach, thyroid, endometrium, prostate, skin, esophagus, and bone marrow cancer. In some embodiments, compositions comprising nanodevices, and any other desired components (e.g., pharmaceutically acceptable carriers, adjuvants and exipients) are administered to the subject. The present invention is not limited by the route of administration. Such administration routes include, but are not limited to, endoscopic, intratracheal, intralesion, percutaneous, intravenous, subcutaneous, and intratumoral administration.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4A shows "targeting and imaging" applications, wherein the nano-device targets neoplastic cells through a cell-surface moiety and is taken into the cell through receptor mediated endocytosis. The tumor 00 is imaged through MRI. FIG. 4B shows "sensing cancer signature" applications, wherein red fluorescence is activated by the presence of the cancer signature (Muc1, Her2, or mutated p53 through quantum dot-like aggregation or loss of 1 quenching). FIG. 4C shows "triggered release of therapeutic" applications, wherein laser light is targeted to red-emitting cells and cleaves photo-labile protecting group from drug (e.g., platinum or Taxol releasing it from dendrimer matrix). FIG. 4D shows "monitoring response to therapy" applications, wherein a drug induces apoptosis in cells, and caspase activity activates green fluorescence. Apoptotic cancer cells turn orange while residual cancer cells remain red. Normal cells induced to apoptose (collateral damage) if they fluoresce green.

GENERAL DESCRIPTION OF THE INVENTION

The present invention relates to novel therapeutic and diagnostic complexes. More particularly, the present invention is directed to dendrimer-based multifunctional compositions and systems for use in disease diagnosis and therapy (e.g. cancer diagnosis and therapy). The compositions and systems generally comprise two or more separate components for targeting, imaging, sensing, and/or triggering release of a therapeutic or diagnostic material and monitoring the response to therapy of a cell or tissue (e.g., a tumor).

For example, the present invention provides nanodevices comprising two or more dendrimers, each complexed with one or more components for targeting, imaging, sensing, and/or triggering release of a therapeutic or diagnostic material and monitoring the response to therapy of a cell or tissue. In some embodiments of the present invention, the nanodevice comprises a core dendrimer complexed (e.g., covalently linked) to other dendrimer subunits containing the above functionalities. The present invention demonstrates that such compositions are non-toxic and present new methods for treating, detecting, and monitoring various physiological conditions. For example, in some embodiments, the nanodevices contain a dendrimer subunit that targets the nanodevice to particular cells or tissues (e.g., contains binding agents that recognize and are specific cellular components). In other embodiments, the nanodevices contain a dendrimer subunit that images a cell, a cellular component, or cellular reactions (e.g., provides a detectable signal upon exposure to the cell, component, or reaction). In yet other embodiments, the nanodevices contain a dendrimer subunit that provides a signature identifying agent such that, directly or indirectly, the presence of a cell or cellular condition is identified (e.g., identifying a cancer cell through interaction of the signature identifying agent with a cancer-specific factor). In still further embodiments, the nanodevices contain a dendrimer subunit that provides a therapeutic or diagnostic agent for delivery or release into a cell or subject.

Figure 3:
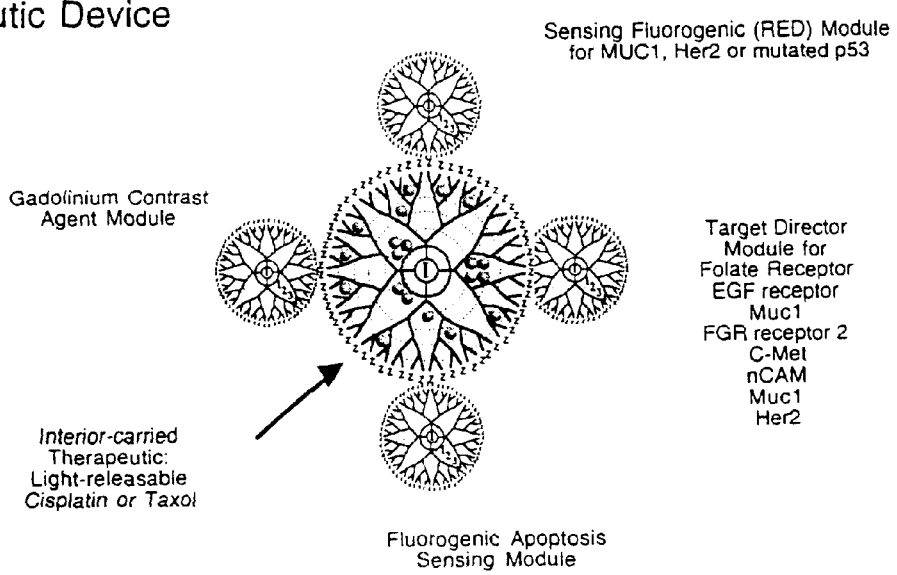
FIG. 3 shows a component structure of nanodevices for breast and colon cancer in some embodiments of the present invention.
Figure 3:
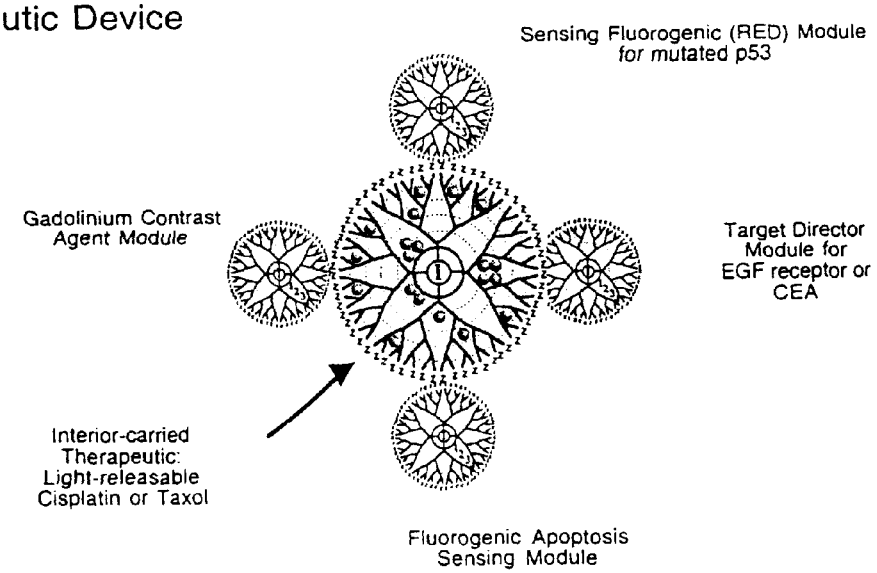
Figure 4:
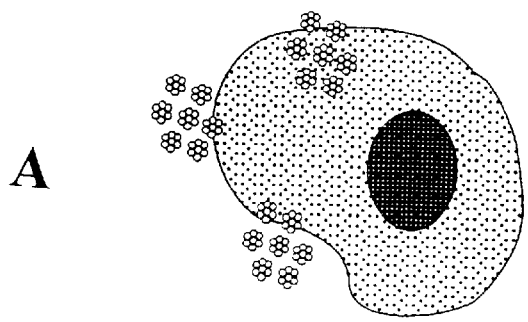
FIGS. 4A–D show functions of therapeutic nanodevices in some embodiment of the present invention.
Figure 4:
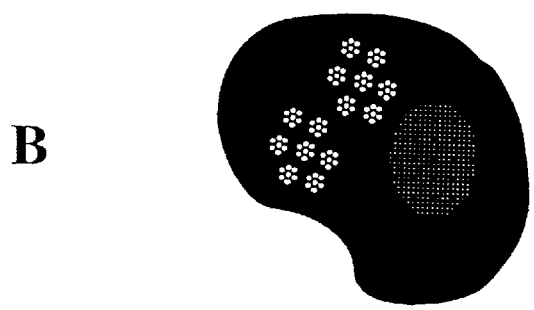
Figure 4:
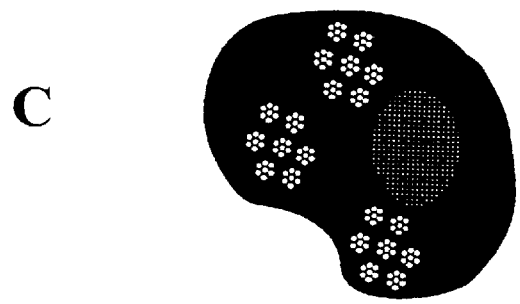
Figure 4:
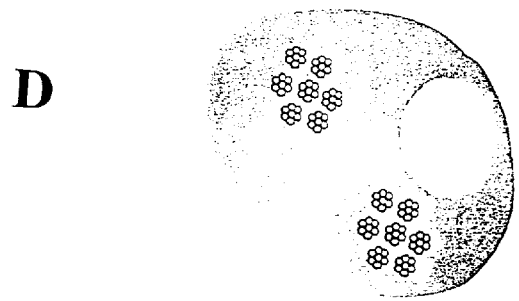

Thus, the present invention provides a variety of useful therapeutic and diagnostic compositions for treating and characterizing cells or subjects with various pathologies or physiological conditions. The nanodevices of the present invention comprises any number of dendrimer components to give the desired functionality. For example, in cancer therapy, the present invention provides nanodevices that comprise a core dendrimer covalently linked to individual dendrimer units comprising signature identifying agents, imaging agents, therapeutic agents, targeting agents, and monitoring agents, respectively. For example, for breast cancer (See e.g., FIG. 3 showing complexes for use in breast and colon cancer; and FIG. 4 as described above), the core dendrimer is complexed with a first dendrimer comprising a gadolinium contrast agent for imaging the tissue by MRI, a second dendrimer comprising a therapeutic agent (e.g., Taxol or cisplatin) for treating the cancer, a third dendrimer comprising a ligand for binding to a folate receptor for targeting the cancer cells, a fourth dendrimer comprising a fluorogenic component for detecting mutated p53 protein for identifying the cancer signature, and a fifth dendrimer comprising a fluorogenic marker of apoptosis to monitor treatment with the therapeutic agent. In some embodiments, the core dendrimer comprises any of the desired components. In yet other embodiments, two or more of the functionalities are provided on a single dendrimer.

In preferred embodiments, of the present invention, libraries of individual dendrimers comprising the above functionalities are created for use in generating any desired nanodevice complexes. For example, libraries of dendrimers each containing one of a host of therapeutic agents are created. The same procedure is conducted for target agents, imaging agents, and the like. Such libraries provide the ability to mix-and-match components to generate the optimum therapeutic or diagnostic complexes for a desired application. The nanodevices may be generated rationally, or may be generated randomly and screened for desired activities. Thus, the present invention provides non-toxic systems with a wide range of therapeutic and diagnostic uses.

Definitions

To facilitate an understanding of the present invention, a number of terms and phrases are defined below:

As used herein, the term "dendrimer complex" refers to a complex comprising two or more dendrimers in physical association with one another (e.g., covalent or non-covalent attachment to one another). For example, two dendrimers covalently linked to one another (e.g., directly or through a linking group) provide a dendrimer complex.

As used herein, the term "agent" refers to a composition that possesses a biologically relevant activity or property. Biologically relevant activities are activities associated with biological reactions or events or that allow the detection, monitoring, or characterization biological reactions or events. Biologically relevant activities include, but are not limited to, therapeutic activities (e.g., the ability to improve biological health or prevent the continued degeneration associated with an undesired biological condition), targeting activities (e.g., the ability to bind or associate with a biological molecule or complex), monitoring activities (e.g., the ability to monitor the progress of a biological event or to monitor changes in a biological composition), imaging activities (e.g., the ability to observe or otherwise detect biological compositions or reactions), and signature identifying activities (e.g., the ability to recognize certain cellular compositions or conditions and produce a detectable response indicative of the presence of the composition or condition). The agents of the present invention are not limited to these particular illustrative examples. Indeed any useful agent may be used including agents that deliver or destroy biological materials, cosmetic agents, and the like. In preferred embodiments of the present invention, the agent or agents are associated with at least one dendrimer (e.g., incorporated into the dendrimer, surface exposed on the dendrimer, etc.). In some embodiments of the present invention, two or more dendrimers are present in a composition where any one dendrimer may have an agent that "is different than" an agent of another dendrimer. "Different than" refers to agents that are distinct from one another in chemical makeup and/or functionality.

As used herein, the term "nanodevice" refers to small (e.g., invisible to the unaided human eye) compositions containing or associated with one or more "agents." In its simplest form, the nanodevice consists of a physical composition (e.g., a dendrimer) associated with at least one agent that provides biological functionality (e.g., a therapeutic agent). However, the nanodevice may comprise additional components (e.g., additional dendrimers and/or agents). In preferred embodiments of the present invention, the physical composition of the nanodevice comprises at least one dendrimer and a biological functionality is provided by at least one agent associated with a dendrimer.

The term "biologically active," as used herein, refers to a protein or other biologically active molecules (e.g., catalytic RNA) having structural, regulatory, or biochemical functions of a naturally occurring molecule.

The term "agonist," as used herein, refers to a molecule which, when interacting with an biologically active molecule, causes a change (e.g., enhancement) in the biologically active molecule, which modulates the activity of the biologically active molecule. Agonists may include proteins, nucleic acids, carbohydrates, or any other molecules which bind or interact with biologically active molecules. For example, agonists can alter the activity of gene transcription by interacting with RNA polymerase directly or through a transcription factor.

The terms "antagonist" or "inhibitor," as used herein, refer to a molecule which, when interacting with a biologically active molecule, blocks or modulates the biological activity of the biologically active molecule. Antagonists and inhibitors may include proteins, nucleic acids, carbohydrates, or any other molecules that bind or interact with biologically active molecules. Inhibitors and antagonists can effect the biology of entire cells, organs, or organisms (e.g., an inhibitor that slows tumor growth).

The term "modulate," as used herein, refers to a change in the biological activity of a biologically active molecule. Modulation can be an increase or a decrease in activity, a change in binding characteristics, or any other change in the biological, functional, or immunological properties of biologically active molecules.

The term "gene" refers to a nucleic acid (e.g., DNA) sequence that comprises coding sequences necessary for the production of a polypeptide or precursor. The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' non-translated sequences. The sequences that are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "antisense" is used in reference to DNA or RNA sequences that are complementary to a specific DNA or RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter which permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labelled "A" and the antibody will reduce the amount of labelled A bound to the antibody.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA seginent(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "gene transfer system" refers to any means of delivering a composition comprising a nucleic acid sequence to a cell or tissue. For example, gene transfer systems include, but are not limited to vectors (e.g., retroviral, adenoviral, adeno-associated viral, and other nucleic acid-based delivery systems), microinjection of naked nucleic acid, and polymer-based delivery systems (e.g., liposome-based and metallic particle-based systems). As used herein, the term "viral gene transfer system" refers to gene transfer systems comprising viral elements (e.g., intact viruses and modified viruses) to facilitate delivery of the sample to a desired cell or tissue. As used herein, the term "adenovirus gene transfer system" refers to gene transfer systems comprising intact or altered viruses belonging to the family Adenoviridae.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fuision, retroviral infection, and biolistics.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The term "test compound" refers to any chemical entity, pharmaceutical, drug, and the like that can be used to treat or prevent a disease, illness, sickness, or disorder of bodily function. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables).

As used herein, the terms "photosensitizer," and "photodynamic dye," refer to materials which undergo transformation to an excited state upon exposure to a light quantum (hv). Examples of photosensitizers and photodynamic dyes include, but are not limited to, Photofrin 2, benzoporphyrin, m-tetrahydroxyphenylchlorin, tin etiopurpurin, copper benzochlorin, and othier porphyrins.

DETAILED DESCRIPTION OF THE INVENTION

The present invention provides novel systems and compositions for the treatment and monitoring of diseases (e.g., cancer). For example, the present invention provides systems and compositions that target, image, and sense pathophysiological defects, provide the appropriate therapeutic based on the diseased state, monitor the response to the delivered therapeutic, and identify residual disease. In preferred embodiments of the present invention, the compositions are small enough to readily enter a patient's or subjects cells.

In preferred embodiments, the systems and compositions of the present invention are used in treatment and monitoring during cancer therapy. However, the systems and compositions of the present invention find use in the treatment and monitoring of a variety of disease states or other physiological conditions, and the present invention is not limited to use with any particular disease state or condition. Other disease states that find particular use with the present invention include, but are not limited to, cardiovascular disease, inflammatory disease, and other proliferative disorders.

In preferred embodiments, the present invention provides nanodevices comprising dendrimer subunits. In preferred embodiments, the nanodevices are limited to a few hundred nanometers in diameter to facilitate internalization into cells.

Preferred embodiments of the present invention provide a composition comprising two or more different dendrimer structures, each including at least one functional component, including, but not limited to, therapeutic agents, biological monitoring components, biological imaging components, targeting components, and components to identify the specific signature of cellular abnormalities. These components ultimately form a therapeutic and/or diagnostic complexes in which each of the different components is located within a distinct dendrimer carrier. As such, the therapeutic nanodevice or complex is made up of at least two separate dendrimer carriers being specifically complexed with or covalently linked to at least one of the other dendrimer compositions of the complexes.

The following discussion describes individual component parts of the nanodevice and methods of making and using the same in some embodiments of the present invention. To illustrate the design and use of the systems and compositions of the present invention, the discussion focuses on specific embodiments of the use of the compositions in the treatment and monitoring of breast adenocarcinoma and colon adenocarcinoma. These specific embodiments are intended only to illustrate certain preferred embodiments of the present invention and are not intended to limit the scope thereof In these embodiments, the nanodevices of the present invention target the neoplastic cells through cell-surface moieties and are taken up by the tumor cell for example through receptor mediated endocytosis. The imaging component of the device allows the tumor to be imaged for example through the use of MRI. In those devices containing a sensing component, red fluorescence is activated by the presence of the particular cancer signature (e.g., Muc1, Her2 or mutated p53). This allows a triggered release of a therapeutic agent contained in the therapeutic component of the nanodevice. The release is facilitated by the therapeutic component being attached to a labile protecting group, such as, for example, cisplatin being attached to a photolabile protecting group that becomes released by laser light directed at those cells emitting the color of fluorescence activated as mentioned above (e.g., red-emitting) cells. Optionally the therapeutic device also may have a component to monitor the response of the tumor to therapy. For example, where the drug induces apoptosis of the cell, the caspase activity of the cells may be used to activate a green fluorescence. This allows apoptotic cells to turn orange, (combination of red and green) while residual cells remain red. Any normal cells that are induced to undergo apoptosis in collateral damage fluoresce green.

As is clear from the above example, the use of the compositions of the present invention facilitates non-intrusive sensing, signaling, and intervention for cancer. Since specific protocols of molecular alterations in cancer cells are identified using this technique, non-intrusive sensing through the dendritic molecules is achieved and may then be employed automatically against various tumor phenotypes. If the polymer array approach is employed, the targeting, sensing, and therapeutic conjugates are interchanged to address varied tumor types or different pathophysiological alterations. Thus, the array approach provides common, interchangeable therapeutic platforms that transcend any single type of tumor or cellular abnormality.

I. Dendrimers

Figure 1:
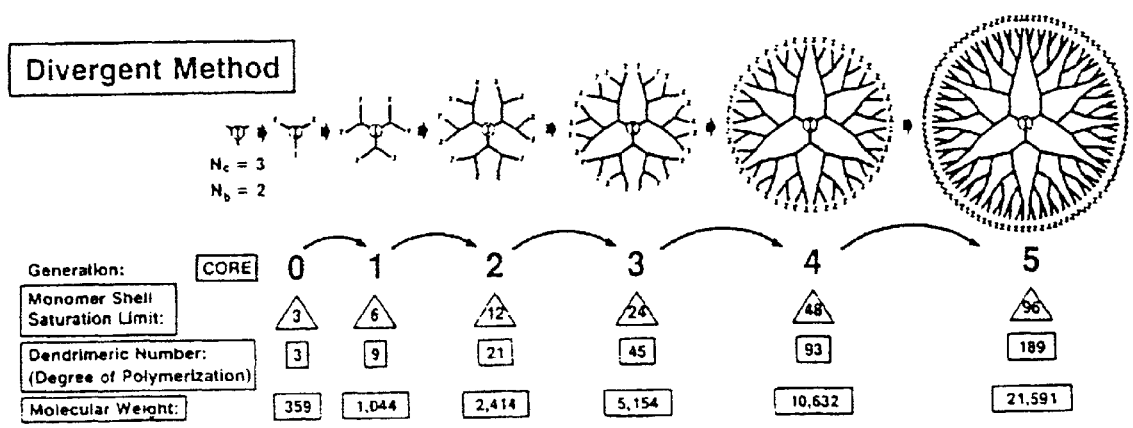
FIG. 1 shows several generations of spherical, dendritic polymers, with each generation increasing the size, molecular weight and number of primary amine groups on the surface of the polymer.

In preferred embodiments of the present invention, the nanodevices comprises dendrimers. Dendrimeric polymers have been described extensively (See, Tomalia, Advanced Materials 6:529 [1994]; Angew, Chem. Int. Ed. Engl., 29:138 [1990]; incorporated herein by reference in their entireties). Dendrimers polymers are synthesized as defined spherical structures typically ranging from 1 to 20 nanometers in diameter. Several generations of polyamidoamine (B-alanine subunit) dendrimers are shown in FIG. 1. Molecular weight and the number of terminal groups increase exponentially as a function of generation (the number of layers) of the polymer. Different types of dendrimers can be synthesized based on the core structure that initiates the polymerization process.

The dendrimer core structures dictate several characteristics of the molecule such as the overall shape, density and surface functionality (Tomalia et al., Chem. Int. Ed. Engl., 29:5305 [1990]. Spherical dendrimers have ammonia as a trivalent initiator core or ethylenediamine (EDA) as a tetravalent initiator core. Recently described rod-shaped dendrimers (Yin et al., J. Am. Chem. Soc., 120:2678 [1998]) use polyethyleneimine linear cores of varying lengths; the longer the core, the longer the rod. Dendritic macromolecules are available commercially in kilogram quantities and are produced under current good manufacturing processes (GMP) for biotechnology applications.

Dendrimers may be characterized by a number of techniques including, but not limited to, electrospray-ionization mass spectroscopy, $^{13}C$ nuclear magnetic resonance spectroscopy, high performance liquid chromatography, size exclusion chromatography with multi-angle laser light scattering, capillary electrophoresis and gel electrophoresis. These tests assure the uniformity of the polymer population and are important for monitoring quality control of dendrimer manufacture for GMP applications and in vivo usage. Extensive studies have been completed with dendrimers and show no evidence of toxicity when administered intravenously in in vivo studies (Roberts et al., J. Biomed. Mat. Res., 30:53 [1996] and Boume et al., J. Magn. Reson. Imag., 6:305 [1996]).

Numerous U.S. Patents describe methods and compositions for producing dendrimers. Examples of some of these patents are given below in order to provide a description of some dendrimer compositions that may be useful in the present invention, however it should be understood that these are merely illustrative examples and numerous other similar dendrimer compositions could be used in the present invention.

U.S. Pat. No. 4,507,466, U.S. Pat. No. 4,558,120, U.S. Pat. No. 4,568,737, and U.S. Pat. No. 4,587,329 each describe methods of making dense star polymers with terminal densities greater than conventional star polymers. These polymers have greater/more uniform reactivity than conventional star polymers, i.e. 3rd generation dense star polymers. These patents further describe the nature of the amidoamine dendrimers and the 3-dimensional molecular diameter of the dendrimers.

U.S. Pat. No. 4,631,337 describes hydrolytically stable polymers. U.S. Pat. No. 4,694,064 describes rod-shaped dendrimers. U.S. Pat. No. 4,713,975 describes dense star polymers and their use to characterize surfaces of viruses, bacteria and proteins including enzymes. Bridged dense star polymers are described in U.S. Pat. No. 4,737,550. U.S. Pat. No. 4,857,599 and U.S. Pat. No. 4,871,779 describe dense star polymers on immobilized cores useful as ion-exchange resins, chelation resins and methods of making such polymers.

U.S. Pat. No. 5,338,532 is directed to starburst conjugates of dendrimer(s) in association with at least one unit of carried agricultural, pharmaceutical or other material. This patent describes the use of dendrimers to provide means of delivery of high concentrations of carried materials per unit polymer, controlled delivery, targeted delivery and/or multiple species such as e.g., drugs antibiotics, general and specific toxins, metal ions, radionuclides, signal generators, antibodies, interleukins, hormones, interferons, viruses, viral fragments, pesticides, and antimicrobials.

Other useful dendrimer type compositions are described in U.S. Pat. No. 5,387,617, U.S. Pat. No. 5,393,797, and U.S. Pat. No. 5,393,795 in which dense star polymers are modified by capping with a hydrophobic group capable of providing a hydrophobic outer shell. U.S. Pat. No. 5,527,524 discloses the use of amino terminated dendrimers in antibody conjugates.

The use of dendrimers as metal ion carriers is described in U.S. Pat. No. 5,560,929. U.S. Pat. No. 5,773,527 discloses non-crosslinked polybranched polymers having a combburst configuration and methods of making the same. U.S. Pat. No. 5,631,329 describes a process to produce polybranched polymer of high molecular weight by forming a first set of branched polymers protected from branching; grafting to a core; deprotecting first set branched polymer, then forming a second set of branched polymers protected from branching and grafting to the core having the first set of branched polymers, etc.

U.S. Pat. No. 5,902,863 describes dendrimer networks containing lipophilic organosilicone and hydrophilic polyanicloamine nanscopic domains. The networks are prepared from copolydendrimer precursors having PAMAM (hydrophilic) or polyproyleneimine interiors and organosilicon outer layers. These dendrimers have a controllable size, shape and spatial distribution. They are hydrophobic dendrimers with an organosilicon outer layer that can be used for specialty membrane, protective coating, composites containing organic organometallic or inorganic additives, skin patch delivery, absorbants, chromatography personal care products and agricultural products.

U.S. Pat. No. 5,795,582 describes the use of dendrimers as adjutants for influenza antigen. Use of the dendrimers produces antibody titer levels with reduced antigen dose. U.S. Pat. No. 5,898,005 and U.S. Pat. No. 5,861,319 describe specific immunobinding assays for determining concentration of an analyte. U.S. Pat. No. 5,661,025 provides details of a self-assembling polynucleotide delivery system comprising dendrimer polycation to aid in delivery of nucleotides to target site. This patent provides methods of introducing a polynucleotide into a eukaryotic cell in vitro comprising contacting the cell with a composition comprising a polynucleotide and a dendrimer polyeation noncovalently coupled to the polynucleotide.

Dendrimer-antibody conjugates for use in in vitro diagnostic applications has previously been demonstrated (Singh et al., Clin. Chem., 40:1845 [1994]), for the production of dendrimer-chelant-antibody constructs, and for the development of boronated dendrimer-antibody conjugates (for neutron capture therapy); each of these latter compounds may be used as a cancer therapeutic (Wu et al., Bioorg. Med. Chem. Lett., 4:449 [1994]; Wiener et al., Magn. Reson. Med. 31:1 [1994]; Barth et al., Bioconjugate Chem. 5:58 [1994]; and Barth et al.).

Some of these conjugates have also been employed in the magnetic resonance imaging of tumors (Wu et al., [1994] and Wiener et al., [1994], supra). Results from this work have documented that, when administered in vivo, antibodies can direct dendrimer-associated therapeutic agents to antigen-bearing tumors. Dendrimers also have been shown to specifically enter cells and carry either chemotherapeutic agents or genetic therapeutics. In particular, studies show that cisplatin encapsulated in dendrimer polymers has increased efficacy and is less toxic than cisplatin delivered by other means (Duncan and Malik, Control Rel. Bioact. Mater. 23:105 [1996]).

Dendrimers have also been conjugated to fluorochromes or molecular beacons and shown to enter cells. They can then be detected within the cell in a manner compatible with sensing apparatus for evaluation of physiologic changes within cells (Baker et al., Anal. Chem. 69:990 [1997]). Finally, dendrimers have been constructed as differentiated block copolymers where the outer portions of the molecule may be digested with either enzyme or light-induced catalysis (Urdea and Hom, Science 261:534 [1993]). This would allow the controlled degradation of the polymer to release therapeutics at the disease site and could provide a mechanism for an external trigger to release the therapeutic agents.

Figure 2:
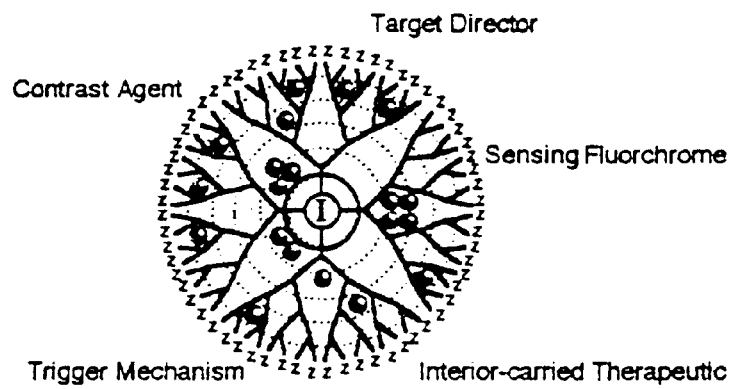
FIG. 2 shows different options for design of dendrimer-based nanodevices.
Figure 2:
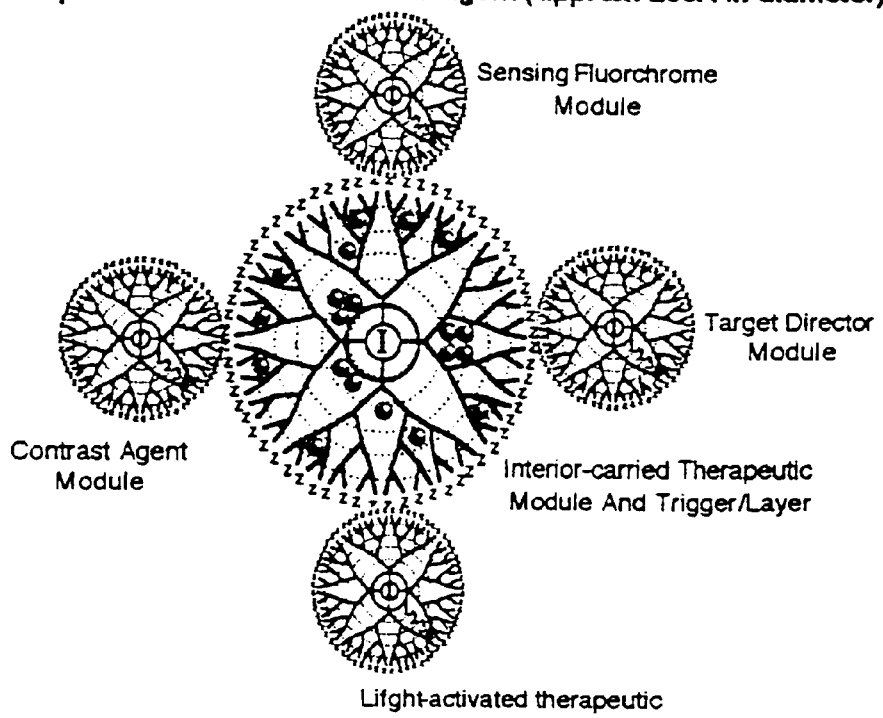

While single dendrimers have been shown to contain these particular functions, to date, there has been no demonstration of a device that encompasses more than one of these modalities in a specific configuration. The present invention provides such nanodevices, wherein two or more dendrimers, each with a specific functionality are combined into a single complex. For example, preferred complexes of the present invention are constructed from individual dendrimer modules around a core dendrimer. This provides a core-shell dendrimer or a cluster molecule as shown in FIG. 2. Prior to the construction of the multi-dendrimer complex, separate conjugates for each of the different activities, e.g., one dendrimer conjugate for sensing, one for targeting and another for therapeutic carrier are produced. These different dendrimer modules are then clustered together and covalently linked in a manner that yields a single therapeutic device or complex.

In this approach, one dendrimer acts as a core around which other shell-type dendrimers are covalently attached. In a preferred embodiment, the core molecule is an amineterminated dendrimer. The shell reagent dendrimers possess carboxylic acid/ester groups that allow covalent attachment by amide formation to the core. A highly concentrated mix of amino-terminated dendrimers with different functional groups of the same or higher generation are then added to a core dendrimer. A cluster then forms by amide formation between the terminal amine groups of the core and the free terminal carboxylic acid groups of the functional outer dendrimers. A limited number of bonds can form between the core dendrimer and each outer-layer dendrimer because of sterically induced stoichiometries. In some embodiments, a molar excess of the outer-layer dendrimer is used to bias the reaction so that each outer core dendrimer reacts only with a single core molecule.

II. Therapeutic Agents

A wide range of therapeutic agents find use with the present invention. Any therapeutic agent that can be associated with a dendrimer may be delivered using the methods, systems, and compositions of the present invention. To illustrate delivery of therapeutic agents, the following discussion focuses mainly on the delivery of cisplatin and taxol for the treatment of cancer. Also discussed are various photodynamic therapy compounds, and various antimicrobial compounds.

i. Cisplatin and Taxol

Cisplatin and Taxol have a well-defined action of inducing apoptosis in tumor cells (See e.g., Lanni et al., Proc. Natl. Acad. Sci., 94:9679 [1997]; Tortora et al., Cancer Research 57:5107 [1997]; and Zaffaroni et al., Brit. J. Cancer 77:1378 [1998]). However, treatment with these and other chemotherapeutic agents is difficult to accomplish without incurring significant toxicity. The agents currently in use are generally poorly water soluble, quite toxic, and given at doses that affect normal cells as wells as diseased cells. For example, paclitaxel (Taxol), one of the most promising anticancer compounds discovered, is poorly soluble in water. Paclitaxel has shown excellent antitumor activity in a wide variety of tumor models such as the B16 melanoma, L1210 leukemias, MX-1 mammary tumors, and CS-1 colon tumor xenografts. However, the poor aqueous solubility of paclitaxel presents a problem for human administration. Accordingly, currently used paclitaxel formulations require a cremaphor to solubilize the drug. The human clinical dose range is 200–500 mg. This dose is dissolved in a 1:1 solution of ethanol:cremaphor and diluted to one liter of fluid given intravenously. The cremaphor currently used is polyethoxylated castor oil. It is given by infusion by dissolving in the cremaphor mixture and diluting with large volumes of an aqueous vehicle. Direct administration (e.g., subcutaneous) results in local toxicity and low levels of activity. Thus, there is a need for more efficient and effective delivery systems for these chemotherapeutic agents.

The present invention overcomes these problems by providing methods and compositions for specific drug delivery. The present invention also provides the ability to administer combinations of agents (e.g., two or more different therapeutic agents) to produce an additive effect. The use of multiple agent may be used to counter disease resistance to any single agent. For example, resistance of some cancers to single drugs (taxol) has been reported (Yu et al., Molecular Cell. 2:581 [1998]). Experiments conducted during the development of the present invention have demonstrated that cisplatin, conjugated to dendrimers, is even able to efficiently kill cancer cells that are resistant to cisplatin (See, Example 4). Although an understanding of the mechanism is not necessary to practice the present invention and the present invention is not so limited, it is contemplated that the dendrimer conjugates prevent multidrug resistance channels from pumping the cisplatin out of the cell.

The present invention also provides the opportunity to monitor therapeutic success following delivery of cisplatin and/or Taxol to a subject. For example, measuring the ability of these drugs to induce apoptosis in vitro is reported to be a marker for in vivo efficacy (Gibb, Gynecologic Oncology 65:13 [1997]). Therefore, in addition to the targeted delivery of either one or both of these drugs to provide effective anti-tumor therapy and reduce toxicity, the effectiveness of the therapeutic can be gauged by techniques of the present invention that monitor the induction of apoptosis. Importantly, both therapeutics are active against a wide-range of tumor types including, but not limited to, breast cancer and colon cancer (Akutsu et al., Eur. J. Cancer 31A:2341 [1995]).

Although the above discussion describes two specific agents, any pharmaceutical that is routinely used in a cancer therapy context finds use in the present invention. In treating cancer according to the invention, the therapeutic component of the nanodevice may comprise compounds including, but not limited to, adriamycin, 5-fluorouracil, etoposide, camptothecin, actinomycin-D, mitomycin C, or more preferably, cisplatin. The agent may be prepared and used as a combined therapeutic composition, or kit, by combining it with the immunotherapeutic agent, as described herein.

In some embodiments of the present invention, the dendrimer systems further comprise one or more agents that directly cross-link nucleic acids (e.g., DNA) to facilitate DNA damage leading to a synergistic, antineoplastic agents of the present invention. Agents such as cisplatin, and other DNA alkylating agents may be used. Cisplatin has been widely used to treat cancer, with efficacious doses used in clinical applications of 20 mg/M$^2$ for 5 days every three weeks for a total of three courses. The nanodevice may be delivered via any suitable method, including, but not limited to, injection intravenously, subcutaneously, intratumorally, intraperitoneally, or topically (e.g., to mucosal surfaces).

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 Mg/M$^2$ at 21 day intervals for adriamycin, to 35–50 Mg/M$^2$ for etoposide intravenously or double the intravenous dose orally.

Agents that disrupt the synthesis and fidelity of nucleic acid precursors and subunits also lead to DNA damage and find use as chemotherapeutic agents in the present invention. A number of nucleic acid precursors have been developed. Particularly useful are agents that have undergone extensive testing and are readily available. As such, agents such as 5-fluorouracil (5-FU) are preferentially used by neoplastic tissue, making this agent particularly useful for targeting to neoplastic cells. The doses delivered may range from 3 to 15 mg/kg/day, although other doses may vary considerably according to various factors including stage of disease, amenability of the cells to the therapy, amount of resistance to the agents and the like.

The anti-cancer therapeutic agents that find use in the present invention are those that are amenable to incorporation into dendrimeric structures or are otherwise associated with dendrimer structures such that they can be delivered into a subject, tissue, or cell without loss of fidelity of its anticancer effect. For a more detailed description of cancer therapeutic agents such as a platinum complex, verapamil, podophyllotoxin, carboplatin, procarbazine, mechlorethamine, cyclophosphamide, camptothecin, ifosfamide, melphalan, chlorambucil, bisulfan, nitrosurea, adriamycin, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate and other similar anti-cancer agents, those of skill in the art are referred to any number of instructive manuals including, but not limited to, the Physician's Desk reference and to Goodman and Gilman's "Pharmaceutical Basis of Therapeutics" ninth edition, Eds. Hardman et al., 1996.

In preferred embodiments, the drugs are preferably attached to the nanodevice with photocleavable linkers. For example, several heterobifunctional, photocleavable linkers that find use with the present invention are described by Ottl et al. (Ottl et al., Bioconjugate Chem., 9:143 [1998]). These linkers can be either water or organic soluble. They contain an activated ester that can react with amines or alcohols and an epoxide that can react with a thiol group. In between the two groups is a 3,4-dimethoxy6-nitrophenyl photoisomerization group, which, when exposed to near-ultraviolet light (365 nm), releases the amine or alcohol in intact form. Thus, the therapeutic agent, when linked to the compositions of the present invention using such linkers, may be released in biologically active or activatable form through exposure of the target area to near-ultraviolet light.

In an exemplary embodiment, the alcohol group of taxol is reacted with the activated ester of the organic-soluble linker. This product in turn is reacted with the partially-thiolated surface of appropriate dendrimers (the primary amines of the dendrimers can be partially converted to thiol-containing groups by reaction with a sub-stoichiometric amount of 2-iminothiolano). In the case of cisplatin, the amino groups of the drug are reacted with the water-soluble form of the linker. If the amino groups are not reactive enough, a primary amino-containing active analog of cisplatin, such as Pt(II) sulfadiazine dichloride (Pasani et al., Inorg. Chim. Acta 80:99 [1983] and Abel et al, Eur. J. Cancer 9:4 [1973]) can be used. Thus conjugated, the drug is inactive and will not harm normal cells. When the conjugate is localized within tumor cells, it is exposed to laser light of the appropriate near-UV wavelength, causing the active drug to be released into the cell.

Similarly, in other embodiments of the present invention, the amino groups of cisplatin (or an analog thereof) is linked with a very hydrophobic photocleavable protecting group, such as the 2-nitrobenzyloxycarbonyl group (Pillai, V.N.R. Synthesis: 1–26 [1980]). With this hydrophobic group attached, the drug is loaded into and very preferentially retained by the hydrophobic cavities within the PAMAM dendrimer (See e.g., Esfand et al., Pharm. Sci., 2:157 [1996]), insulated from the aqueous environment. When exposed to near-LV light (about 365 nm), the hydrophobic group is cleaved, leaving the intact drug. Since the drug itself is hydrophilic, it diffuses out of the dendrimer and into the tumor cell, where it initiates apoptosis.

An alternative to photocleavable linkers are enzyme cleavable linkers. A number of photocleavable linkers have been demonstrated as effective anti-tumor conjugates and can be prepared by attaching cancer therapeutics, such as doxorubicin, to water-soluble polymers with appropriate short peptide linkers (See e.g., Vasey et al., Clin. Cancer Res., 5:83 [1999]). The linkers are stable outside of the cell, but are cleaved by thiolproteases once within the cell. In a preferred embodiment, the conjugate PK1 is used. As an alternative to the photocleavable linker strategy, enzyme-degradable linkers, such as Gly-Phe-Leu-Gly may be used.

The present invention is not limited by the nature of the therapeutic technique. For example, other conjugates that find use with the present invention include, but are not limited to, using conjugated boron dusters for BNCT (Capala et al., Bioconjugate Chem., 7:7 [1996]), the use of radioisotopes, and conjugation of toxins such as ricin to the nanodevice.

ii. Photodynamic Therapy

Photodynamic therapeutic agents may also be used as therapeteutic agents in the present invention. In some embodiments, the dendrimeric compositions of the present invention containing photodynamic compounds are illuminated, resulting in the production of singlet oxygen and free radicals that diffuse out of the fiberless radiative effector to act on the biological target (e.g., tumor cells or bacterial cells). Some preferred photodynamic compounds include, but are not limited to, those that can participate in a type II photochemical reaction:

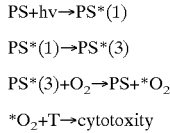

where PS=photosenstizer, PS*(1)=excited singlet state of PS, PS*(3)=excited triplet state of PS, hv=light quantum, *$O_2$=excited singlet state of oxygen, and T=biological target. Other photodynamic compounds useful in the present invention include those that cause cytotoxity by a different mechanism than singlet oxygen production (e.g., copper benzochlorin, Selman, et al., Photochem. Photobiol., 57:681–85 [1993], incorporated herein by reference). Examples of photodynamic compounds that find use in the present invention include, but are not limited to Photofrin 2, phtalocyanins (See e.g., Brasseur et al., Photochem. Photobiol., 47:705–11 [1988]), benzoporphyrin, tetrahydroxyphenylporphyrins, naphtalocyanines (See e.g., Firey and Rodgers, Photochem. Photobiol., 45:535–38 [1987]), sapphyrins (Sessler et al., Proc. SPIE, 1426:318–29 [1991]), porphinones (Chang et al., Proc. SPIE, 1203:281–86 [1990]), tin etiopurpurin, ether substituted porphyrins (Pandey et al., Photochem. Photobiol., 53:65–72 [1991]), and cationic dyes such as the phenoxazines (See e.g., Cincotta et al., SPIE Proc., 1203:202–10 [1990]).

In other embodiments, toxic agents that directly produce free radicals (i.e., do not produce singlet oxygen) are incorporated into the fiberless radiative effectors during polymerization. This approach allows for larger and longer lived fiberless radiative effectors and will not be limited by local oxygen supplies. Such toxic agents include, but are not limited to 2-methyl-4-nitro-quinoline-N-oxide (Aldrich) and 4,4-dinitro-(2,2) bipyridinyl-N,N dioxide (Aldrich), which produce hydroxyl radicals when illuminated with 360–400 nm light (Botchway et al., Photochem. Photobiol. 67(7):635–40 [1998]); malachite green and isofuran blue (Molecular Probes), which produce hydroxyl radicals upon stimulation with about 630 nm light (Jay et al., PNAS 91:2659 [1994]; Haugland, Handbook of Fluorescent Probes and Research Chemicals, 6th ed., Molecular Probes, Eugene, Oreg. [1994]); potassium nitrosylpentachlororuthenate (Molecular Probes) (abs=516 nm), Roussin's black salt and Roussin's red salt (abs 313–546 nm), serve as sources of NO which is toxic to cells (Murphy et al., Neuropharm. 33:1375–85 [1994]; Bourassa et al., JACS 119:2853–60 [1997]); and other photolytic nitric oxide and hydroxyl donors (De Leo and Ford, JACS 121:1980–81 [1999]).

iii. Antimicrobial Therapeutic Agents

Antimicrobial therapeutic agents may also be used as therapeteutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins, antisense nucleic acids, membrane disruptive agents and the like, used alone or in combination. Indeed, any type of antibiotic may be used including, but not limited to, anti-bacterial agents, anti-viral agents, anti-fungal agents, and the like.

III. Signature Identifying Agents

In certain embodiments, the nano-devices of the present invention contain one or more signature identifying agents that are activated by, or are able to interact with, a signature component ("signature"). In preferred embodiments, the signature identifying agent is an antibody, preferably a monoclonal antibody, that specifically binds the signature (e.g., cell surface molecule specific to a cell to be targeted).

In some embodiments of the present invention, tumor cells are identified. Tumor cells have a wide variety of signatures, including the defined expression of cancer-specific antigens such as Muc1, HER-2 and mutated p53 in breast cancer. These act as specific signatures for the cancer, being present in 30% (HER-2) to 70% (mutated p53) of breast cancers. In a preferred embodiment, a nanodevice of the present invention comprises a monoclonal antibody that specifically binds to a mutated version of p53 that is present in breast cancer.

In some embodiments of the present invention, cancer cells expressing susceptibility genes are identified. For example, in some embodiments, there are two breast cancer susceptibility genes that are used as specific signatures for breast cancer: BRCA1 on chromosome 17 and BRCA2 on chromosome 13. When an individual carries a mutation in either BRCA1 or BRCA2, they are at an increased risk of being diagnosed with breast or ovarian cancer at some point in their lives. These genes participate in repairing radiation-induced breaks in double-stranded DNA. It is thought that mutations in BRCA1 or BRCA2 might disable this mechanism, leading to more errors in DNA replication and ultimately to cancerous growth.

In addition, the expression of a number of different cell surface receptors find use as targets for the binding and uptake of the nano-device. Such receptors include, but are not limited to, EGF receptor, folate receptor, FGR receptor 2, and the like.

In some embodiments of the present invention, changes in gene expression associated with chromosomal abborations are the signature component. For example, Burkitt lymphoma results from chromosome translocations that involve the Myc gene. A chromosome translocation means that a chromosome is broken, which allows it to associate with parts of other chromosomes. The classic chromosome translocation in Burkitt lymophoma involves chromosome 8, the site of the Myc gene. This changes the pattern of Myc expression, thereby disrupting its usual function in controlling cell growth and proliferation.

In other embodiments, gene expression associated with colon cancer are identified as the signature component. Two key genes are known to be involved in colon cancer: MSH2 on chromosome 2 and MLH1 on chromosome 3. Normally, the protein products of these genes help to repair mistakes made in DNA replication. If the MSH2 and MLH1 proteins are mutated, the mistakes in replication remain unrepaired, leading to damaged DNA and colon cancer. MEN1 gene, involved in multiple endocrine neoplasia, has been known for several years to be found on chromosome 11, was more finely mapped in 1997, and serves as a signature for such cancers. In preferred embodiments of the present invention, an antibody specific for the altered protein or for the expressed gene to be detected is complexed with nanodevices of the present invention.

In yet another embodiment, adenocarcinoma of the colon has defined expression of CEA and mutated p53, both well-documented tumor signatures. The mutations of p53 in some of these cell lines are similar to that observed in some of the breast cancer cells and allows for the sharing of a p53 sensing component between the two nanodevices for each of these cancers (i.e., in assembling the nanodevice, dendrimers comprising the same signature identifying agent may be used for each cancer type). Both colon and breast cancer cells may be reliably studied using cell lines to produce tumors in nude mice, allowing for optimization and characterization in animals.

From the discussion above it is clear that there are many different tumor signatures that find use with the present invention, some of which are specific to a particular type of cancer and others which are promiscuous in their origin. The present invention is not limited to any particular tumor signature or any other disease-specific signature. For example, tumor suppressors that find use as signatures in the present invention include, but are not limited to, p53, Muc1, CEA, p16, p21, p27, CCAM, RB, APC, DCC, NF-1, NF-2, WT-1, MEN-1, MEN-II, p73, VHL, FCC and MCC.

IV. Biological Imaging Component

In some embodiments of the present invention, the nanodevice comprises at least one dendrimer-based nanoscopic building block that can be readily imaged. The present invention is not limited by the nature of the imaging component used. In some embodiments of the present invention, imaging modules comprise surface modifications of quantum dots (See e.g., Chan and Nie, Science 281:2016 [1998]) such as zinc sulfide-capped cadmium selenide coupled to biomolecules (Sooklal, Adv. Mater., 10:1083 [1998]).

However, in preferred embodiments, the imaging module comprises dendrimers produced according to the "nanocomposite" concept (Balogh et al., Proc. of ACS PMSE 77:118 [1997] and Balogh and Tomalia, J. Am. Che. Soc., 120:7355 [1998]). In these embodiments, dendrimers are produced by reactive encapsulation, where a reactant is preorganized by the dendrimer template and is then subsequently immobilized in/on the polymer molecule by a second reactant. Size, shape, size distribution and surface functionality of these nanoparticles are determined and controlled by the dendritic macromolecules. These materials have the solubility and compatibility of the host and have the optical or physiological properties of the guest molecule (i.e., the molecule that permits imaging). While the dendrimer host may vary according to the medium, it is possible to load the dendrimer hosts with different compounds and at various guest concentration levels. Complexes and composites may involve the use of a variety of metals or other inorganic materials. The high electron density of these materials considerably simplifies the imaging by electron microscopy and related scattering techniques. In addition, properties of inorganic atoms introduce new and measurable properties for imaging in either the presence or absence of interfering biological materials. In some embodiments of the present invention, encapsulation of gold, silver, cobalt, iron atoms/molecules and/or organic dye molecules such as fluorescein are encapsulated into dendrimers for use as nanoscopi composite labels/tracers, although any material that facilitates imaging or detection may be employed.

In some embodiments of the present invention, imaging is based on the passive or active observation of local differences in density of selected physical properties of the investigated complex matter. These differences may be due to a different shape (e.g., mass density detected by atomic force microscopy), altered composition (e.g. radiopaques detected by X-ray), distinct light emission (e.g., fluorochromes detected by spectrophotometry), different diffraction (e.g., electron-beam detected by TEM), contrasted absorption (e.g., light detected by optical methods), or special radiation emission (e.g., isotope methods), etc. Thus, quality and sensitivity of imaging depend on the property observed and on the technique used. The imaging techniques for cancerous cells have to provide sufficient levels of sensitivity to is observe small, local concentrations of selected cells. The earliest identification of cancer signatures requires high selectivity (i.e., highly specific recognition provided by appropriate targeting) and the highest possible sensitivity.

A. Magnetic Resonance Imaging

Once the targeted nanodevice has attached to (or been internalized into) tumor cells, one or more modules on the device serve to image its location. Dendrimers have already been employed as biomedical imaging agents, perhaps most notably for magnetic resonance imaging (MRI) contrast enhancement agents (See e.g., Wiener et al., Mag. Reson. Med. 31:1 [1994]; an example using PAMAM dendrimers). These agents are typically constructed by conjugating chelated paramagnetic ions, such as Gd(III)-diethylenetriaminepentaacetic acid (Gd(III)-DTPA), to water-soluble dendrimers. Other paramagnetic ions that may be useful in this context of the include, but are not limited to, gadolinium, manganese, copper, chromium, iron, cobalt, erbium, nickel, europium, technetium, indium, samarium, dysprosium, ruthenium, ytterbium, yttrium, and holmium ions and combinations thereof. In some embodiments of the present invention, the dendrimer is also conjugated to a targeting group, such as epidermal growth factor (EGF), to make the conjugate specifically bind to the desired cell type (e.g., in the case of EGF, EGFR-expressing tumor cells). In a preferred embodiment of the present invention, DTPA is attached to dendrimers via the isothiocyanate of DTPA as described by Wiener (Wiener et al., Mag. Reson. Med. 31:1 [1994]).

Dendrimeric MRI agents are particularly effective due to the polyvalency, size and architecture of dendrimers, which results in molecules with large proton relaxation enhancements, high molecular relaxivity, and a high effective concentration of paramagnetic ions at the target site. Dendrimeric gadolinium contrast agents have even been used to differentiate between benign and malignant breast tumors using dynamic MRI, based on how the vasculature for the latter type of tumor images more densely (Adam et al., Ivest. Rad. 31:26 [1996]). Thus, MRI provides a particularly useful imaging system of the present invention.

B. Microscopic Imaging

Static structural microscopic imaging of cancerous cells and tissues has traditionally been performed outside of the patient. Classical histology of tissue biopsies provides a fine illustrative example, and has proven a powerful adjunct to cancer diagnosis and treatment. After removal, a specimen is sliced thin (e.g., less than 40 microns), stained, fixed, and examined by a pathologist. If images are obtained, they are most often 2-D transmission bright-field projection images. Specialized dyes are employed to provide selective contrast, which is almost absent from the unstained tissue, and to also provide for the identification of aberrant cellular constituents. Quantifying sub-cellular structural features by using computer-assisted analysis, such as in nuclear ploidy determination, is often confounded by the loss of histologic context owing to the thinness of the specimen and the overall lack of 3-D information. Despite the limitations of the static imaging approach, it has been invaluable to allow for the identification of neoplasia in biopsied tissue. Furthermore, its use is often the crucial factor in the decision to perform invasive and risky combinations of chemotherapy, surgical procedures, and radiation treatments, which are often accompanied by severe collateral tissue damage, complications, and even patient death.

The nanodevices of the present invention allow functional microscopic imaging of tumors and provide improved methods for imaging. The methods find use in vivo, in vitro, and ex vivo. For example, in one embodiment of the present invention, dendrimers of the present invention are designed to emit light or other detectable signals upon exposure to light. Although the labeled dendrimers may be physically smaller than the optical resolution limit of the microscopy technique, they become self-luminous objects when excited and are readily observable and measurable using optical techniques. In some embodiments of the present invention, sensing fluorescent biosensors in a microscope involves the use of tunable excitation and emission filters and multiwavelength sources (Farkas et al., SPEI 2678:200 [1997]). In embodiments where the imaging agents are present in deeper tissue, longer wavelengths in the Near-infrared (NMR) are used (See e.g., Lester et al., Cell Mol. Biol. 44:29 [1998]). Dendrimeric biosensing in the Near-IR has been demonstrated with dendrimeric biosensing antenna-like architectures (Shortreed et al., J. Phys. Chem., 101:6318 [1997]). Biosensors that find use with the present invention include, but are not limited to, fluorescent dyes and molecular beacons.

In some embodiments of the present invention, in vivo imaging is accomplished using functional imaging techniques. Functional imaging is a complementary and potentially more powerful techniques as compared to static structural imaging. Functional imaging is best known for its application at the macroscopic scale, with examples including functional Magnetic Resonance Imaging (fMRI) and Positron Emission Tomography (PET). However, functional microscopic imaging may also be conducted and find use in in vivo and ex vivo analysis of living tissue. Functional microscopic imaging is an efficient combination of 3-D imaging, 3-D spatial multispectral volumetric assignment, and temporal sampling: in short a type of 3-D spectral microscopic movie loop. Interestingly, cells and tissues autofluoresce. When excited by several wavelengths, providing much of the basic 3-D structure needed to characterize several cellular components (e.g., the nucleus) without specific labeling. Oblique light illumination is also useful to collect structural information and is used routinely. As opposed to structural spectral microimaging, functional spectral microimaging may be used with biosensors, which act to localize physiologic signals within the cell or tissue. For example, in some embodiments of the present invention, biosensor-comprising dendrimers of the present invention are used to image upregulated receptor families such as the folate or EGF classes. In such embodiments, functional biosensing therefore involves the detection of physiological abnormalities relevant to carcinogenesis or malignancy, even at early stages. A number of physiological conditions may be imaged using the compositions and methods of the present invention including, but not limited to, detection of nanoscopic dendrimeric biosensors for pH, oxygen concentration, $Ca^{2+}$ concentration, and other physiologically relevant analytes.

V. Biological Monitoring Component

The biological monitoring or sensing component of the nanodevice of the present invention is one which that can monitor the particular response in the tumor cell induced by an agent (e.g., a therapeutic agent provided by the therapeutic component of the nanodevice). While the present invention is not limited to any particular monitoring system, the invention is illustrated by methods and compositions for monitoring cancer treatments. In preferred embodiments of the present invention, the agent induces apoptosis in cells and monitoring involves the detection of apoptosis. In particular embodiments, the monitoring component is an agent that fluoresces at a particular wavelength when apoptosis occurs. For example, in a preferred embodiment, caspase activity activates green fluorescence in the monitoring component. Apoptotic cancer cells, which have turned red as a result of being targeted by a particular signature with a red label, turn orange while residual cancer cells remain red. Normal cells induced to undergo apoptosis (e.g., through collateral damage), if present, will fluoresce green.

In these embodiments, fluorescent groups such as fluorescein are employed in the monitoring component. Fluorescein is easily attached to the dendrimer surface via the isothiocyanate derivatives, available from Molecular Probes, Inc. This allows the nanodevices to be imaged with the cells via confocal microscopy.

Sensing of the effectiveness of the nanodevices is preferably achieved by using fluorogenic peptide enzyme substrates. For example, apoptosis caused by the therapeutic agents results in the production of the peptidase caspase-1 (ICE). Calbiochem sells a number of peptide substrates for this enzyme that release a fluorescent moiety. A particularly useful peptide for use in the present invention is:

MCA-Tyr-Glu-Val-Asp-Gly-Trp-Lys-(DNP)-$NH_2$ (SEQ ID NO: 1)

where MCA is the (7-methoxycoumarin-4-yl)acetyl and DNP is the 2,4-dinitrophenyl group (Talanian et al., J. Biol. Chem., 272: 9677 [1997]). In this peptide, the MCA group has greatly attenuated fluorescence, due to fluorogenic resonance energy transfer (FRET) to the DNP group. When the enzyme cleaves the peptide between the aspartic acid and glycine residues, the MCA and DNP are separated, and the MCA group strongly fluoresces green (excitation maximum at 325 nm and emission maximum at 392 nm).

In preferred embodiments of the present invention, the lysine end of the peptide is linked to the nanodevice, so that the MCA group is released into the cytosol when it is cleaved. The lysine end of the peptide is a useful synthetic handle for conjugation because, for example, it can react with the activated ester group of a bifunctional linker such as Mal-PEG-OSu. Thus the appearance of green fluorescence in the target cells produced using these methods provides a clear indication that apoptosis has begun (if the cell already has a red color from the presence of aggregated quantum dots, the cell turns orange from the combined colors).

Additional fluorescent dyes that find use with the present invention include, but are not limited to, acridine orange, reported as sensitive to DNA changes in apoptotic cells (Abrams et al., Development 117:29 [1993]) and cis-parinaric acid, sensitive to the lipid peroxidation that accompanies apoptosis (Hockenbery et al., Cell 75:241 [1993]). It should be noted that the peptide and the fluorescent dyes are merely exemplary. It is contemplated that any peptide that effectively acts as a substrate for a caspase produced as a result of apoptosis finds use with the present invention.

VI. Targeting Components

As described above, another component of the present invention is that the nanodevice compositions are able to specifically target a particular cell type (e.g., tumor cell). Generally, the nanodevice targets neoplastic cells through a cell surface moiety and is taken into the cell through receptor mediated endocytosis.

Any moiety known to be located on the surface of target cells (e.g. tumor cells) finds use with the present invention. For example, an antibody directed against such a moiety targets the compositions of the present invention to cell surfaces containing the moiety. Alternatively, the targeting moiety may be a ligand directed to a receptor present on the cell surface or vice versa. Similarly, vitamins also may be used to target the therapeutics of the present invention to a particular cell.

In some embodiments of the present invention, the targeting moiety may also function as a signatures component. For example, tumor specific antigens including, but not limited to, carcinoembryonic antigen, prostate specific antigen, tyrosinase, ras, a sialyly lewis antigen, erb, MAGE-1, MAGE-3, BAGE, MN, gp100, gp75, p97, proteinase 3, a mucin, CD81, CID9, CD63; CD53, CD38, CO-029, CA125, GD2, GM2 and O-acetyl GD3, M-TAA, M-fetal or M-urinary find use with the present invention. Alternatively the targeting moiety may be a tumor suppressor, a cytokine, a chemokine, a tumor specific receptor ligand, a receptor, an inducer of apoptosis, or a differentiating agent.

Tumor suppressor proteins contemplated for targeting include, but are not limited to, p16, p21, p27, p53, p73, Rb, Wilns tumor (WT-1), DCC, neurofibromatosis type 1 (NF-1), von Hippel-Lindau (VHL) disease tumor suppressor, Maspin, Brush-1, BRCA-1, BRCA-2, the multiple tumor suppressor (MTS), gp95/p97 antigen of human melanoma, renal cell carcinoma-associated G250 antigen, KS 1/4 pan-carcinoma antigen, ovarian carcinoma antigen (CA125), prostate specific antigen, melanoma antigen gp75, CD9, CD63, CD53, CD37, R2, CD81, CO029, TI-1, L6 and SAS. Of course these are merely exemplary tumor suppressors and it is envisioned that the present invention may be used in conjunction with any other agent that is or becomes known to those of skill in the art as a tumor suppressor.

In preferred embodiments of the present invention targeting is directed to factors expressed by an oncogene. These include, but are not limited to, tyrosine kinases, both membrane-associated and cytoplasmic forms, such as members of the Src family, serine/threonine kinases, such as Mos, growth factor and receptors, such as platelet derived growth factor (PDDG), SMALL GTPases (G proteins) including the ras family, cyclin-dependent protein kinases (cdk), members of the myc family members including c-myc, N-myc, and L-myc and bcl-2 and family members.

Cytokines that may be targeted by the present invention include, but are not limited to, IL-1, IL-2, IL-3, IL-4, IL-5, IL-6, IL-7, IL-8, IL-9, IL-10, ILA 1, IL-12, IL-13, IL-14, IL-15, TNF, GMCSF, β-interferon and γ-interferon. Chemokines that may be used include, but are not limited to, M1P1α, M1P1β, and RANTES.

Enzymes that may be targeted by the present invention include, but are not limited to, cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase, and human thymidine kinase.

Receptors and their related ligands that find use in the context of the present invention include, but are not limited to, the folate receptor, adrenergic receptor, growth hormone receptor, luteinizing hormone receptor, estrogen receptor, epidermal growth factor receptor, fibroblast growth factor receptor, and the like.

Hormones and their receptors that find use in the targeting aspect of the present invention include, but are not limited to, growth hormone, prolactin, placental lactogen, luteinizing hormone, foilicle-stimulating hormone, chorionic gonadotropin, thyroid-stimulating hormone, leptin, adrenocorticotropin (ACTH), angiotensin I, angiotensin II, β-endorphin, β-melanocyte stimulating hormone (β-MSH), cholecystokinin, endothelin I, galanin, gastric inhibitory peptide (GIP), glucagon, insulin, amylin, lipotropins, GLP-1 (7–37) neurophysins, and somatostatin.

In addition, the present invention contemplates that vitamins (both fat soluble and non-fat soluble vitamins) placed in the targeting component of the nanodevice may be used to target cells that have receptors for, or otherwise take up these vitamins. Particularly preferred for this aspect are the fat soluble vitamins, such as vitamin D and its analogues, vitamin E, Vitamin A, and the like or water soluble vitamins such as Vitamin C, and the like.

In some embodiments of the present invention, any number of cancer cell targeting groups are attached to dendrimers. The targeting dendrimers are, in turn, conjugated to a core dendrimer. Thus the nanodevice of the present invention is such that it is specific for targeting cancer cells (i.e., much more likely to attach to cancer cells and not to healthy cells). In addition, the polyvalency of dendrimers allows the attachment of polyethylene glycol (PEG) or polyethyloxazoline (PEOX) chains to help increase the blood circulation time and decrease the immunogenicity of the conjugates.

In preferred embodiments of the present invention, targeting groups are conjugated to dendrimers with either short (e.g., direct coupling), medium (e.g. using small-molecule bifunctional linkers such as SPDP, sold by Pierce Chemical Company), or long (e.g., PEG bifunctional linkers, sold by Shearwater Polymers) linkages. Since dendrimers have surfaces with a large number of functional groups, more than one targeting group may be attached to each dendrimer. As a result, there are multiple binding events between the dendrimer and the target cell. In these embodiments, the dendrimers have a very high affinity for their target cells via this "cooperative binding" or polyvalent interaction effect.

For steric reasons, the smaller the ligands, the more can be attached to the surface of a dendrimer. Recently, Wiener reported that dendrimers with attached folic acid would specifically accumulate on the surface and within tumor cells expressing the high-affinity folate receptor (hFR) (Wiener et al., Invest. Radiol., 32:748 [1997]). The hFR receptor is expressed or upregulated on epithelial tumors, including breast cancers. Control cells lacking hFR showed no significant accumulation of folate-derivatized dendrimers. Folic acid can be attached to full generation PAMAM dendrimers via a carbodiimide coupling reaction. Folic acid is a good targeting candidate for the dendrimers, with its small size and a simple conjugation procedure.

A larger, yet still relatively small ligand is epidermal growth factor (EGF), a single-chain peptide with 53 amino acid residues. It has been shown that PAMAM dendrimers conjugated to EGF with the linker SPDP bind to the cell surface of human glioma cells and are endocytosed, accumulating in lysosomes (Casale et al., Bioconjugate Chem., 7:7 [1996]). Since EGF receptor density is up to 100 times greater on brain tumor cells compared to normal cells, EGF provides a useful targeting agent for these kinds of tumors. Since the EGF receptor is also overexpressed in breast and colon cancer, EGF may be used as a targeting agent for these cells as well. Similarly, the fibroblast growth factor receptors (EGER) also bind the relatively small polypeptides (FGF), and many are known to be expressed at high levels in breast tumor cell lines (particularly FGF1, 2 and 4) (Penault-Llorca et al., Int. J. Cancer 61:170 [1995]).

In preferred embodiments of the present invention, the targeting moiety is an antibody or antigen binding fragment of an antibody (e.g., Fab units). For example, a well-studied antigen found on the surface of many cancers (including breast HER2 tumors) is glycoprotein p185, which is exclusively expressed in malignant cells (Press et al., Oncogene 5:953 [1990]). Recombinant humanized anti-HER2 monoclonal antibodies (rhuMabHER2) have even been shown to inhibit the growth of HER2 overexpressing breast cancer cells, and are being evaluated (in conjunction with conventional chemotherapeutics) in phase III clinical trials for the treatment of advanced breast cancer (Pegram et al., Proc. Am. Soc. Clin. Oncol., 14:106 [1995]). Park and Papahadjopoulos have attached Fab fragments of rhuMabHER2 to small unilamellar liposomes, which then can be loaded with the chemotherapeutic doxorubicin (dox) and targeted to HER2 overexpressing tumor xenografts (Park et al., Cancer Lett., 118:153 [1997] and Kirpotin et al., Biochem., 36:66 [1997]). These dox-loaded "immunoliposomes" showed increased cytotoxicity against tumors compared to corresponding non-targeted dox-loaded liposomes or free dox, and decreased systemic toxicity compared to free dox.

Antibodies can be generated to allow for the targeting of antigens or immunogens (e.g., tumor, tissue or pathogen specific antigens) on various biological targets (e.g., pathogens, tumor cells, normal tissue). Such antibodies include, but are not limited to polyclonal, monoclonal, chimeric, single chain, Fab fragments, and an Fab expression library.

In some preferred embodiments, the antibodies recognize tumor specific epitopes (e.g., TAG-72 (Kjeldsen et al., Cancer Res. 48:2214–2220 [1988]; U.S. Pat. Nos. 5,892,020; 5,892,019; and 5,512,443); human carcinoma antigen (U.S. Pat. Nos. 5,693,763; 5,545,530; and 5,808,005); TP1 and TP3 antigens from osteocarcinoma cells (U.S. Pat. No. 5,855,866); Thomsen-Friedenreich (TF) antigen from adenocarcinoma cells (U.S. Pat. No. 5,110,911); "KC-4 antigen" from human prostrate adenocarcinoma (U.S. Pat. Nos. 4,708,930 and 4,743,543); a human colorectal cancer antigen (U.S. Pat. No. 4,921,789); CA125 antigen from cystadenocarcinoma (U.S. Pat. No. 4,921,790); DF3 antigen from human breast carcinoma (U.S. Pat. Nos. 4,963,484 and 5,053,489); a human breast tumor antigen (U.S. Pat. No. 4,939,240); p97 antigen of human melanoma (U.S. Pat. No. 4,918,164); carcinoma or orosomucoid-related antigen (CORA)(U.S. Pat. No. 4,914,021); a human pulmonary carcinoma antigen that reacts with human squamous cell lung carcinoma but not with human small cell lung carcinoma (U.S. Pat. No. 4,892,935); T and Tn haptens in glycoproteins of human breast carcinoma (Springer et al., Carbohydr. Res. 178:271–292 [1988]), MSA breast carcinoma glycoprotein termed (Tjandra et al., Br. J. Surg. 75:811–817 [1988]); MFGM breast carcinoma antigen (Ishida et al., Tumor Biol. 10:12–22 [1989]); DU-PAN-2 pancreatic carcinoma antigen (Lan et al., Cancer Res. 45:305–310 [1985]); CA125 ovarian carcinoma antigen (Hanisch et al., Carbohydr. Res. 178:29–47 [1988]); YH206 lung carcinoma antigen (Hinoda et al., (1988) Cancer J. 42:653–658 [1988]). Each of the foregoing references are specifically incorporated herein by reference.

In other preferred embodiments, the antibodies recognize specific pathogens (e.g., *Legionella peomophilia, Mycobacterium tuberculosis, Clostridium tetani, Hemophilus influenzae, Neisseria gonorrhoeae, Treponema pallidum, Bacillus anthracis, Vibrio cholerae, Borrelia burgdorferi, Cornebacterium diphtheria, Staphylococcus aureus*, human papilloma virus, human immunodeficiency virus, rubella virus, polio virus, and the like).

Various procedures known in the art are used for the production of polyclonal antibodies. For the production of antibody, various host animals can be immunized by injection with the peptide corresponding to the desired epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies, any technique that provides for the production of antibody molecules by continuous cell lines in culture may be used (See e.g., Harlow and Lane, *Antibodies: A Laboratory Manual, Cold Spring Harbor Laboratory Press*, Cold Spring Harbor, N.Y.). These include, but are not limited to, the hybridoma technique originally developed by Köhler and Milstein (Köhler and Milstein, Nature 256:495–497 [1975]), as well as the trioma technique, the human B-cell hybridoma technique (See e.g., Kozbor et al. Immunol. Today 4:72 [1983]), and the EBV-hybridoma technique to produce human monoclonal antibodies (Cole et al., in *Monoclonal Antibodies and Cancer Therapy*, Alan R. Liss, Inc., pp. 77–96 [1985]).

In an additional embodiment of the invention, monoclonal antibodies can be produced in germn-free animals utilizing recent technology (See e.g., PCT/US90/02545). According to the invention, human antibodies may be used and can be obtained by using human hybridomas (Cote et al., Proc. Natl. Acad. Sci. U.S.A.80:2026–2030 [1983]) or by transforming human B cells with EBV virus in vitro (Cole et al., in *Monoclonal Antibodies and Cancer Therapy*, Alan R. Liss, pp. 77–96 [1985]).

According to the invention, techniques described for the production of single chain antibodies (U.S. Pat. No. 4,946,778; herein incorporated by reference) can be adapted to produce specific single chain antibodies. An additional embodiment of the invention utilizes the techniques described for the construction of Fab expression libraries (Huse et al., Science 246:1275–1281 [1989]) to allow rapid and easy identification of monoclonal Fab fragments with the desired specificity.

Antibody fragments that contain the idiotype (antigen binding region) of the antibody molecule can be generated by known techniques. For example, such fragments include but are not limited to: the F(ab')2 fragment that can be produced by pepsin digestion of the antibody molecule; the Fab' fragments that can be generated by reducing the disulfide bridges of the F(ab')2 fragment, and the Fab fragments that can be generated by treating the antibody molecule with papain and a reducing agent.

In the production of antibodies, screening for the desired antibody can be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.).

The dendrimer systems of the present invention have many advantages over liposomes, such as their greater stability, better control of their size and polydispersity, and generally lower toxicity and immunogenicity (See e.g., Duncan et al, Polymer Preprints 39:180 [1998]). Thus, in some embodiments of the present invention, anti-HER2 antibody fragments, as well as other targeting antibodies are conjugated to dendrimers, as targeting agents for the nanodevices of the present invention.

For breast cancer, the cell surface may be targeted with folic acid, EGF, FGF, and antibodies (or antibody fragments) to the tumor-associated antigens MUC1, cMet receptor and CD56 (NCAM). Once internalized into the cell, the nanodevice binds (via conjugated antibodies) to HER2, MUC1 or mutated p53.

The bifunctional linkers SPDP and SMCC and the longer Mal-PEG-OSu linkers are particularly useful for antibody-dendrimer conjugation. In addition, many tumor cells contain surface lectins that bind to oligosaccharides, with specific recognition arising chiefly from the terminal carbohydrate residues of the latter (Sharon and Lis, Science 246:227 [1989]). Attaching appropriate monosaccharides to nonglycosylated proteins such as BSA provides a conjugate that binds to tumor lectin much more tightly than the free monosaccharide (Monsigny et al., Biochemie 70:1633 [1988]).

Mannosylated PAMAM dendrimers bind mannoside-binding lectin up to 400 more avidly than monomeric mannosides (Page and Roy, Bioconjugate Chem., 8:714 [1997]). Sialylated dendrimers and other dendritic polymers bind to and inhibit a variety of sialate-binding viruses both in vitro and in vivo. By conjugating multiple monosaccharide residues (e.g., $\alpha$-galactoside, for galactose-binding cells) to dendrimers, polyvalent conjugates are created with a high affniity for the corresponding type of tumor cell. The attachment reaction are easily carried out via reaction of the terminal amines with commercially-available $\alpha$-galactosidyl-phenylisothiocyanate. The small size of the carbohydrates allows a high concentration to be present on the dendrimer surface.

A very flexible method to identify and select appropriate peptide targeting groups is the phage display technique (See e.g., Cortese et al., Curr. Opin. Biotechol., 6:73 [1995]), which can be conveniently carried out using commercially available kits. The phage display procedure produces a large and diverse combinatorial library of peptides attached to the surface of phage, which are screened against immobilized surface receptors for tight binding. After the tight-binding, viral constructs are isolated and sequenced to identify the peptide sequences. The cycle is repeated using the best peptides as starting points for the next peptide library. Eventually, suitably high-affinity peptides are identified and then screened for biocompatibility and target specificity. In this way, it is possible to produce peptides that can be conjugated to dendrimers, producing multivalent conjugates with high specificity and affinity for the target cell receptors (e.g., tumor cell receptors) or other desired targets.

Related to the targeting approaches described above is the "pretargeting" approach (See e.g., Goodwin and Meares, Cancer (suppl.) 80:2675 [1997]). An example of this strategy involves initial treatment of the patient with conjugates of tumor-specific monoclonal antibodies and streptavidin. Remaining soluble conjugate is removed from the bloodstream with an appropriate biotinylated clearing agent. When the tumor-localized conjugate is all that remains, a radiolabeled, biotinylated agent is introduced, which in turn localizes at the tumor sites by the strong and specific biotin-streptavidin interaction. Thus, the radioactive dose is maximized in dose proximity to the cancer cells and minimized in the rest of the body where it can harm healthy cells.

It has been shown that if streptavidin molecules bound to a polystyrene well are first treated with a biotinylated dendrimer, and then radiolabeled streptavidinis introduced, up to four of the labeled streptavidin molecules are bound per polystyrene-bound streptavidin (Wilbur et al., Bioconjugate Chem., 9:813 [1998]). Thus, biotinylated dendrimers may be used in the methods of the present invention, acting as a polyvalent receptor for the radiolabel in vivo, with a resulting amplification of the radioactive dosage per bound antibody conjugate. In the preferred embodiments of the present invention, one or more multiply-biotinylated module (s) on the clustered dendrimer presents a polyvalent target for radiolabeled or boronated (Barth et al., Cancer Investigation 14:534 [1996]) avidin or streptavidin, again resulting in an amplified dose of radiation for the tumor cells.

Dendrimers and clustered dendrimers may also be used as clearing agents by, for example, partially biotinylating a dendrimer that has a polyvalent galactose or mannose surface. The conjugate-clearing agent complex would then have a very strong affinity for the corresponding hepatocyte receptors.

In other embodiments of the present invention, an enhanced permeability and retention (EPR) method is used in targeting. The enhanced permeability and retention (EPR) effect is a more "passive" way of targeting tumors (See, Duncan and Sat, Ann. Oncol., 9:39 [1998]). The EPR effect is the selective concentration of macromolecules and small particles in the tumor microenvironment, caused by the hyperpermeable vasculature and poor lymphatic drainage of tumors. The dendrimer compositions of the present invention provide ideal polymers for this application, in that they are relatively rigid, of narrow polydispersity, of controlled size and surface chemistry, and have interior "cargo" space that can carry and then release antitumor drugs. In fact, PAMAM dendrimer-platinates have been shown to accumulate in solid tumors (Pt levels about 50 times higher than those obtained with cisplatin) and have in vivo activity in solid tumor models for which cisplatin has no effect (Malik et al., Proc. Int'l. Symp. Control. Rel. Bioact. Mater., 24:107 [1997] and Duncan et al., Polymer Preprints 39:180 [1998]).

The targeting moieties of the present invention may recognize a variety of other A epitopes on biological targets (e.g., on pathogens). In some embodiments, molecular recognition elements are incorporated to recognize, target or detect a variety of pathogenic organisms including, but not limited to, sialic acid to target HIV (Wies et al., Nature 333: 426 [1988]), influenza (White et al., Cell 56: 725 [1989]), Chlamydia (Infect. Imm. 57: 2378 [1989]), *Neisseria meningitidis, Streptococcus suis*, Salmonella, mumps, newcastle, and various viruses, including reovirus, Sendai virus, and myxovirus; and 9-OAC sialic acid to target coronavirus, encephalomyelitis virus, and rotavirus; non-sialic acid glycoproteins to detect cytomegalovirus (Virology 176: 337 [1990]) and measles virus (Virology 172: 386 [1989]); CD4 (Khatzman et al., Nature 312: 763 [1985]), vasoactive intestinal peptide (Sacerdote et al., J. of Neuroscience Research 18: 102 [1987]), and peptide T (Ruff et al., FEBS Letters 211: 17 [1987]) to target HIV; epidermal growth factor to target vaccinia (Epstein et al., Nature 318: 663 [1985]); acetylcholine receptor to target rabies (Lentz et al., Science 215: 182 [1982]); Cd3 complement receptor to target Epstein-Barr virus (Carel et al., J. Biol. Chem. 265: 12293 [1990]); β-adrenergic receptor to target reovirus (Co et al., Proc. Natl. Acad. Sci. 82: 1494 [1985]); ICAM-1 (Marlin et al., Nature 344: 70 [1990]), N-CAM, and myelin-associated glycoprotein MAb (Shephey et al., Proc. Natl. Acad. Sci. 85: 7743 [1988]) to target rhinovirus; polio virus receptor to target polio virus (Mendelsohn et al., Cell 56: 855 [1989]); fibroblast growth factor receptor to target herpes virus (Kaner et al., Science 248: 1410 [1990]); oligomannose to target *Escherichia coli*; ganglioside $G_{M1}$ to target *Neissetia meningitidis*; and antibodies to detect a broad variety of pathogens (e.g., *Neissetia gonorrhoeae, V. vulnificus, V. parahaemolyticus, V. cholerae*, and *V. alginolyticus*).

In some embodiments of the present invention, the targeting moieties are preferably nucleic acids (e.g., RNA or DNA). In some embodiments, the nucleic acid targeting moieties are designed to hybridize by base pairing to a particular nucleic acid (e.g., chromosomal DNA, mRNA, or ribosomal RNA). In other embodiments, the nucleic acids bind a ligand or biological target. Nucleic acids that bind the following proteins have been identified: reverse transcriptase, Rev and Tat proteins of HIV (Tuerk et al., Gene 137(1):33–9 [1993]); human nerve growth factor (Binkley et al., Nuc. Acids Res. 23(16):3198–205 [1995]); and vascular endothelial growth factor (Jellinek et al., Biochem. 83(34):10450–6 [1994]). Nucleic acids that bind ligands are preferably identified by the SELEX procedure (See e.g., U.S. Pat. Nos. 5,475,096; 5,270,163; and 5,475,096; and in PCT publications WO 97/38134, WO 98/33941, and WO 99/07724, all of which are herein incorporated by reference), although many methods are known in the art.

VII. Synthesis and Conjugation

The present section provides a description of the synthesis and formation of the individual components (i.e., individual dendrimers containing one or more of the components described above) of the nanodevice and the conjugation of such components into a nanodevice (e.g., the conjugation of one or more such dendrimers to a core dendrimer).

Figure 7:
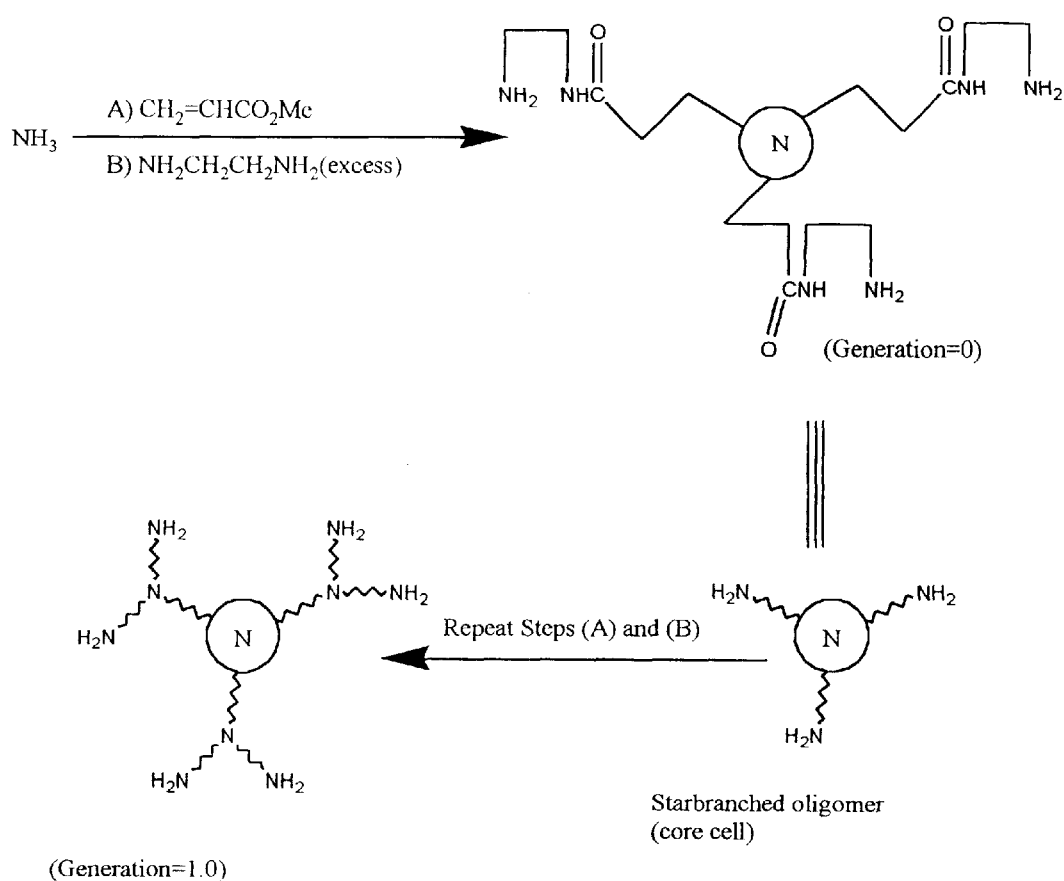
FIG. 7 shows a dendrimer synthesis procedure in some embodiments of the present invention.

In preferred embodiments of the present invention, the preparation of PAMAM dendrimers is performed according to a typical divergent (building up the macromolecule from an initiator core) synthesis. It involves a two-step growth sequence that consists of a Michael addition of amino groups to the double bond of methyl acrylate (MA) followed by the amidation of the resulting terminal carbomethoxy, —($CO_2CH_3$) group, with ethylenediamine (EDA). When ammonia is used as the initiator core reagent, this synthesis may be represented by reactions shown in FIG. 7.

In the first step of this process, ammonia is allowed to react under an inert nitrogen atmosphere with MA (molar ratio: 1:4.25) at 47° C. for 48 hours. The resulting compound is referred to as generation=0, the star-branched PAMAM tri-ester. The next step involves reacting the tri-ester with an excess of EDA to produce the star-branched PAMAM tri-amine (G=O). This reaction is performed under an inert atmosphere (nitrogen) in methanol and requires 48 hours at 0° C. for completion. Reiteration of this Michael addition and amidation sequence produces generation=1.

Preparation of this tri-amine completes the first full cycle of the divergent synthesis of PAMAM dendrimers. Repetition of this reaction sequence results in the synthesis of larger generation (G=1–5) dendrimers (i.e., ester- and amine-terminated molecules, respectively). For example, the second iteration of this sequence produces generation 1, with an hexa-ester and hexa-amine surface, respectively. The same reactions are performed in the same way as for all subsequent generations from 1 to 9, building up layers of branch cells giving a core-shell architecture with precise molecular weights and numbers of terminal groups as shown above. Carboxylate-surfaced dendrimers can be produced by hydrolysis of ester-terminated PAMAM dendrimers, or reaction of succinic anhydride with amine-surfaced dendrimers (e.g., full generation PAMAM, POPAM or POPAM-PAMAM hybrid dendrimers).

Various dendrimers can be synthesized based on the core structure that initiates the polymerization process. These core structures dictate several important characteristics of the dendrimer molecule such as the overall shape, density, and surface functionality (Tomalia et al., Angew. Chem. Int. Ed. Engl., 29:5305 [1990]). Spherical dendrimers derived from ammonia possess trivalent initiator cores, whereas EDA is a tetra-valent initiator core. Recently, rod-shaped dendrimers have been reported which are based upon linear poly(ethyleneimine) cores of varying lengths the longer the core, the longer the rod (Yin et al., J. Am. Chem. Soc., 120:2678 [1998]).

The dendrimers may be characterized for size and uniformity by any suitable analytical techniques. These include, but are not limited to, atomic force microscopy (AFM), electrospray-ionization mass spectroscopy, MALDI-TOF mass spectroscopy, $^{13}C$ nuclear magnetic resonance spectroscopy, high performance liquid chromatography (HPLC) size exclusion chromatography (SEC) (equipped with multi-angle laser light scattering, dual UV and refractive index detectors), capillary electrophoresis and get electrophoresis. These analytical methods assure the uniformity of the dendrimer population and are important in the quality control of dendrimer production for eventual use in in vivo applications. Most importantly, extensive work has been performed with dendrimers showing no evidence of toxicity when administered intravenously (Roberts et al., J. Biomed. Mater. Res., 30:53 [1996] and Boume et al., J. Magnetic Resonance Imaging, 6:305 [1996]).

To produce a single dendritic device possessing the various functional modules required for active sensing, targeting, imaging and therapeutic delivery, multiple PAMAM dendrimer modules, each with an individual differentiated function are covalently bound to form a single device. This involves the synthesis of separate conjugates or nanocomposites for each of the required activities (e.g., one dendrimer conjugate for sensing, one for targeting and another for therapeutic carrier). These different dendrimers are then self-assembled and covalently linked in a manner that yields a single therapeutic device. In certain embodiments, one dendrimer acts as a core around which other dendrimers are covalently (i.e., "clustered dendrimers"). In preferred embodiments, the core dendrimer is a POPAM dendrimer, while the outer dendrimers are PAMAM dendrimers. In yet other embodiments, dendrimers may be complexed to one another without a core dendrimer (e.g., four dendrimers covalently linked to one another in a linear chain).

In one preferred embodiments of the present invention the formation of clustered dendrimers involves the formation of amide bonds between the core and exterior dendrimers using the ester aminolysis technique. The ester aminolysis technique involves reacting various poly(amidoamine) PAMAM dendrimer core reagents with an excess of ester terminated PAMAM dendrimer shell reagents in methanol at 40° C. (See e.g., Uppuluri et al., PMSE 80:55 [1999]). In an alternative embodiment, water is employed as the reaction medium. This method involves the self-assembly of amine terminated core reagents with an excess of carboxylate shell reagent followed by addition of a coupling agent (i.e., carboimide) to produce aminde linkages between the core and the shell components. These reactions take place at room temperature. Such embodiments are preferred when the reactions are conducted in the presence of biomolecules such as antibodies.

Figure 5:
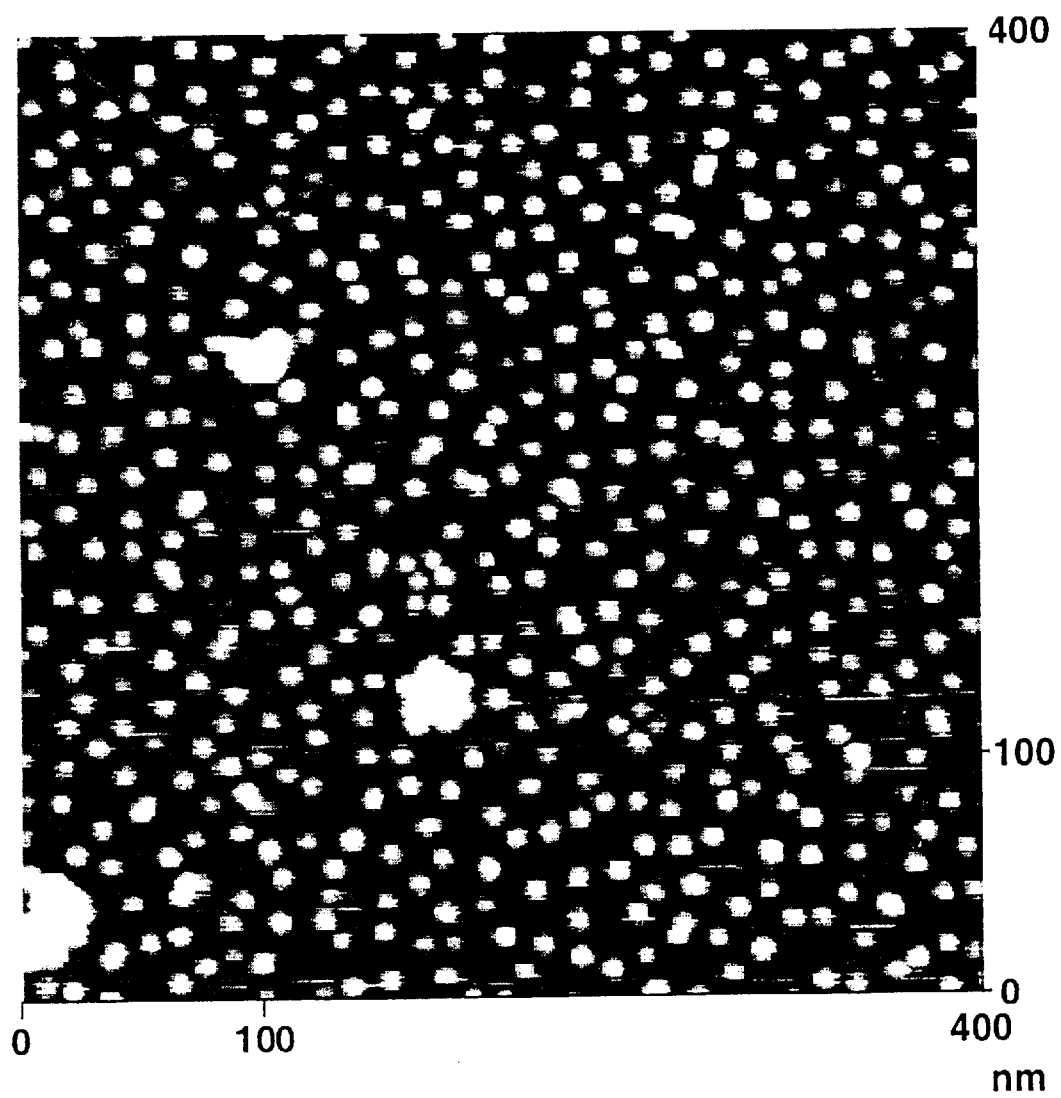
FIG. 5 shows a photograph of an atomic force microscopy (AFM) image of large (generation 9 MW 800 kDA) PAMAM dendritic polymers of the present invention. There is uniformity in size and shape. Three larger, noncovalently bonded clusters of dendrimers also are present in the figure.
Figure 6:
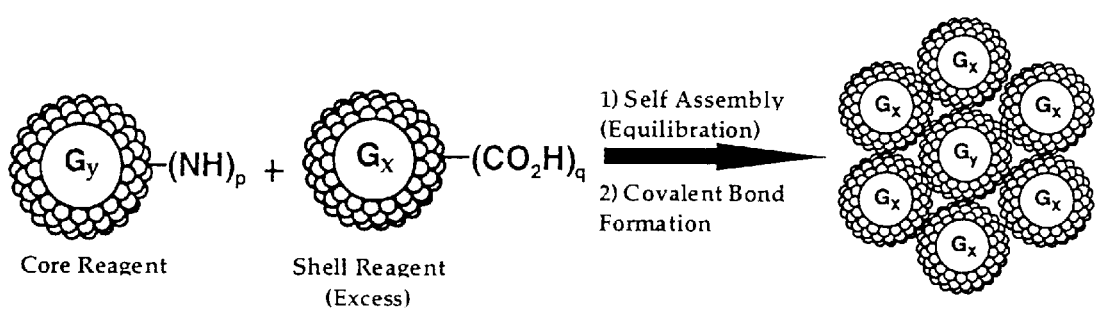
FIG. 6 shows aqueous synthesis of clustered dendrimers in some embodiments of the present invention.

The first step in the aqueous synthesis of these molecules involves self-assembly of the shell dendrimer molecules around a core dendrimer molecule, resulting in the efficient (i.e., maximum) packing of shell molecules around the core. The self-assembled cluster, as shown in FIG. 5, is representative of the precursor used to make the covalently bonded core shell clustered dendrimer. In the next step, using a coupling reagent (such as EDC, a carbodiimide reagent), the core and shell molecules are covalently linked as shown in FIG. 6. The reaction progress is monitored by size exclusion chromatography (SEC) and the loss of carboxylate functionality in the infrared region (FTIR) as well as by $^1H/^{13}C$ NMR and gel electrophoresis. The reaction is normally complete within an hour when run at room temperature.

In some embodiments of the present invention, the size and shape of these higher molecular weight products is measured and compared to individual dendrimers by atomic force microscopy (AFM) and size exclusion chromatography SEC. These techniques demonstrate that core-shell dendrimers are indeed formed. Additional evidence is obtained, as desired, by gel electrophoresis, in which a higher molecular weight product is evident when the reaction is complete. The absolute molecular weight of the clustered dendrimer is determined by MALDI-TOF mass spectroscopy or by SEC equipped with a multi-angle laser light scattering detector (MALLS).

The clustered dendrimer molecules formed by this method have narrow polydispersity by SEC (similar to that of large dendrimers). It takes about 3–4 weeks to convert PAMAM dendrimers of generation 6 to generation 9, but only about 1 day to synthesize clustered dendrimers with similar size, acceptable dispersity and shape (including purification procedures).

For the multi-function clustered dendrimer, any cross-linking reaction problems with the functional groups on the exterior dendrimer modules are circumvented by using standard protecting groups on the side chains that are reacting. Another solution is to use bifunctional linker strategies, e.g., first, reacting the surface of the core amino-surfaced dendrimer with 2-iminothiolane to generate a thiol surface, then reacting the product with maleimide linker groups on the shell dendrimers.

VIII. Evaluation of Anti-Tumor Efficacy and Toxicity of Nanodevice

The anti-tumor effects of various therapeutic agents on cancer cell lines and primary cell cultures may be evaluated using the nanodevices of the present invention. For example, in preferred embodiments, assays are conducted, in vitro, using established tumor cell line models or primary culture cells. The use of fresh tumor cells (as opposed to cultured lines) is preferable for confirmation of toxicity testing and efficacy because it allows more relevant determinations without artifacts induced by tissue culture (e.g., tumor cell selection, etc.).

A. Quantifying the Induction of Apoptosis of Human Tumor Cells In Vitro

In an exemplary embodiment of the present invention, the nanodevices of the present invention are used to assay apoptosis of human tumor cells in vitro. Testing for apoptosis in the cells determines the efficacy of the therapeutic agent. Multiple aspects of apoptosis can and should be measured. These aspects include those described above, as well as aspects including, but are not limited to, measurement of phosphatidylserine (PS) translocation from the inner to outer surface of plasma membrane, measurement of DNA fragmentation, detection of apoptosis related proteins, and measurement of Caspase-3 activity.

B. In Vitro Toxicology

In some embodiments of the present invention, to gain a general perspective into the safety of a particular nanodevice platform or component of that system, toxicity testing is performed. Toxicological information may be derived from numerous sources including, but not limited to, historical databases, in vitro testing, and in vivo animal studies.

In vitro toxicological methods have gained popularity in recent years due to increasing desires for alternatives to animal experimentation and an increased perception to the potential ethical, commercial, and scientific value. In vitro toxicity testing systems have numerous advantages including improved efficiency, reduced cost, and reduced variability between experiments. These systems also reduce animal usage, eliminate confounding systemic effects (e.g., immunity), and control environmental conditions.

Although any in vitro testing system may be used with the present invention, the most common approach utilized for in vitro examination is the use of cultured cell models. These systems include freshly isolated cells, primary cells, or transformed cell cultures. Cell culture as the primary means of studying in vitro toxicology is advantageous due to rapid screening of multiple cultures, usefulness in identifying and assessing toxic effects at the cellular, subcellular, or molecular level. In vitro cell culture methods commonly indicate basic cellular toxicity through measurement of membrane integrity, metabolic activities, and subcellular perturbations. Commonly used indicators for membrane integrity include cell viability (cell count), clonal expansion tests, trypan blue exclusion, intracellular enzyme release (e.g. lactate dehydrogenase), membrane permeability of small ions ($K^1$, $Ca^{2+}$), and intracellular Ala accumulation of small molecules (e.g., $^{51}Cr$, succinate). Subcellular perturbations include monitoring mitochondrial enzyme activity levels via, for example, the MTT test, determining cellular adenine triphosphate (ATP) levels, neutral red uptake into lysosomes, and quantification of total protein synthesis. Metabolic activity indicators include glutathione content, lipid peroxiidation, and lactate/pyruvate ratio.

C. MTT Assay

The MTT assay is a fast, accurate, and reliable methodology for obtaining cell viability measurements. The MTT assay was first developed by Mosmann (Mosmann, J. Immunol. Meth., 65:55 [1983]). It is a simple colorimetric assay numerous laboratories have utilized for obtaining toxicity results (See e.g., Kuhlmann et al., Arch. Toxicol., 72:536 [1998]). Briefly, the mitochondria produce ATP to provide sufficient energy for the cell. In order to do this, the mitochondria metabolize pyruvate to produce acetyl CoA. Within the mitochondria, acetyl CoA reacts with various enzymes in the tricarboxylic acid cycle resulting in subsequent production of ATP. One of the enzymes particularly useful in the MTT assay is succinate dehydrogenase. MTT (3-(4,5-dimethylthiazol-2-yi)-2 diphenyl tetrazolium bromide) is a yellow substrate that is cleaved by succinate dehydrogenase forming a purple formazan product. The alteration in pigment identifies changes in mitochondria function. Nonviable cells are unable to produce formazan, and therefore, the amount produced directly correlates to the quantity of viable cells. Absorbance at 540 nm is utilized to measure the amount of formazan product.

The results of the in vitro tests can be compared to in vivo toxicity tests in order to extrapolate to live animal conditions. Typically, acute toxicity from a single dose of the substance is assessed. Animals are monitored over 14 days for any signs of toxicity (increased temperature, breathing difficulty, death, etc). Traditionally, the standard of acute toxicity is the median lethal dose ($LD_{50}$), which is the predicted dose at which half of the treated population would be killed. The determination of this dose occurs by exposing test animals to a geometric series of doses under controlled conditions. Other tests include subacute toxicity testing, which measures the animal's response to repeated doses of the nanodevice for no longer than 14 days. Subchronic toxicity testing involves testing of a repeated dose for 90 days. Chronic toxicity testing is similar to subchronic testing but may last for over a 90-day period. In vivo testing can also be conducted to determine toxicity with respect to certain tissues. For example, in some embodiments of the present invention tumor toxicity (i.e., effect of the compositions of the present invention on the survival of tumor tissue) is determined (e.g., by detecting changes in the size and/or growth of tumor tissues).

IX. Gene Therapy Vectors

In particular embodiments of the present invention, the nanodevice compositions comprise transgenes for delivery and expression to a target cell or tissue, in vitro, ex vivo, or in vivo. In such embodiments, rather than containing the actual protein, the dendrimer complex comprises an expression vector construct containing, for example, a heterologous DNA encoding a gene of interest and the various regulatory elements that facilitate the production of the particular protein of interest in the target cells.

In some embodiments, the gene is a therapeutic gene that is used, for example, to treat cancer, to replace a defective gene, or a marker or reporter gene that is used for selection or monitoring purposes. In the context of a gene therapy vector, the gene may be a heterologous piece of DNA. The heterologous DNA may be derived from more than one source (i.e., a multigene construct or a fusion protein). Further, the heterologous DNA may include a regulatory sequence derived from one source and the gene derived from a different source.

Tissue-specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Similarly, promoters may be used to target gene expression in other tissues (e.g., insulin, elastin amylase, pdr-1, pdx-1 and glucokinase promoters target to the pancreas; albumin PEPCK, HBV enhancer, alpha fetoproteinapolipoprotein C, alpha-1 antitrypsin, vitellogenin, NF-AB and transthyretin promoters target to the liver; myosin H chain, muscle creatine kinase, dystrophin, calpain p94, skeletal alpha-actin, fast troponin 1 promoters target to skeletal muscle; keratin promoters target the skin; sm22 alpha; SM-α-actin promoters target smooth muscle; CFTR; human cytokeratin 18 (K18); pulmonary surfactant proteins A, B and Q CC-10; P1 promoters target lung tissue; endothelin-1; E-selectin; von Willebrand factor; KDR/flk-1 target the endothelium; tyrosinase targets melanocytes).

The nucleic acid may be either cDNA or genomic DNA. The nucleic acid can encode any suitable therapeutic protein. Preferably, the nucleic acid encodes a tumor suppressor, cytokine, receptor, inducer of apoptosis, or differentiating agent. The nucleic acid may be an antisense nucleic acid. In such embodiments, the antisense nucleic acid may be incorporated into the nanodevice of the present invention outside of the context of an expression vector.

In preferred embodiments, the nucleic acid encodes a tumor suppressor, cytokines, receptors, or inducers of apoptosis. Suitable tumor suppressors include BRCA1, BRCA2, C-CAM, p16, p211 p53, p73, or Rb. Suitable cytokines include GMCSF, IL-1, IL-2, IL-3, IL-4, IL-5, IL6, IL-7, IL-8, IL-9, IL-10, IL-11, IL-12, IL-13, IL-14, IL-15, β-interferon, γ-interferon, or TNF. Suitable receptors include CFTR, EGFR, estrogen receptor, IL-2 receptor, or VEGFR. Suitable inducers of apoptosis include AdE1B, Bad, Bak, Bax, Bid, Bik, Bim, Harakiri, or ICE-CED3 protease.

X. Methods of Combined Therapy

Tumor cell resistance to DNA damaging agents represents a major problem in clinical oncology. The nanodevices of the present invention provide means of ameliorating this problem by effectively administering a combined therapy approach. However, it should be noted that traditional combination therapy may be employed in combination with the nanodevices of the present invention. For example, in some embodiments of the present invention, nanodevices may be used before, after, or in combination with the traditional therapies.

To kill cells, inhibit cell growth, or metastasis, or angiogenesis, or otherwise reverse or reduce the malignant phenotype of tumor cells using the methods and compositions of the present invention in combination therapy, one contacts a "target" cell with the nanodevices compositions described herein and at least one other agent. These compositions are provided in a combined amount effective to kill or inhibit proliferation of the cell. This process may involve contacting the cells with the immunotherapeutic agent and the agent(s) or factor(s) at the same time. This may be achieved by contacting the cell with a single composition or pharmacological formulation that includes both agents, or by contacting the cell with two distinct compositions or formulations, at the same time, wherein one composition includes, for example, an expression construct and the other includes a therapeutic agent.

Alternatively, the nanodevice treatment may precede or follow the other agent treatment by intervals ranging from minutes to weeks. In embodiments where the other agent and immunotherapy are applied separately to the cell, one would generally ensure that a significant period of time did not expire between the time of each delivery, such that the agent and nanodevice would still be able to exert an advantageously combined effect on the cell. In such instances, it is contemplated that cells are contacted with both modalities within about 12–24 hours of each other and, more preferably, within about 6–12 hours of each other, with a delay time of only about 12 hours being most preferred. In some situations, it may be desirable to extend the time period for treatment significantly, however, where several days (2 to 7) to several weeks (1 to 8) lapse between the respective administrations.

In some embodiments, more than one administration of the immunotherapeutic composition of the present invention or the other agent are utilized. Various combinations may be employed, where nanodevice is "A" and the other agent is "B", as exemplified below:

A/B/A, B/A/B, B/B/A, A/A/B, B/A/A, A/B/B, B/B/B/A, B/B/A/B,

A/A/B/B, A/B/A/B, A/B/B/A, B/B/A/A, B/A/B/A, B/A/A/B, B/B/B/A,

A/A/A/B, B/A/A/A, A/B/A/A, A/A/B/A, A/B/B/B, B/A/B/B, B/B/A/B

Other combinations are contemplated. Again, to achieve cell killing, both agents are delivered to a cell in a combined amount effective to kill or disable the cell.

Other factors that may be used in combination therapy with the nanodevices of the present invention include, but are not limited to, factors that cause DNA damage such as γ-rays, X-rays, and/or the directed delivery of radioisotopes to tumor cells. Other forms of DNA damaging factors are also contemplated such as microwaves and UV-irradiation. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells. The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

In preferred embodiments of the present invention, the regional delivery of the nanodevice to patients with cancers is utilized to maximize the therapeutic effectiveness of the delivered agent. Similarly, the chemo- or radiotherapy may be directed to particular, affected region of the subjects body. Alternatively, systemic delivery of the immunotherapeutic composition and/or the agent may be appropriate in certain circumstances, for example, where extensive metastasis has occurred.

In addition to combining the nanodevice with chemo- and radiotherapies, it also is contemplated that traditional gene therapies are used. For example, targeting of p53 or p16 mutations along with treatment of the nanodevices provides an improved anti-cancer treatment. The present invention contemplates the co-treatment with other tumor-related genes including, but not limited to, p21, Rb, APC, DCC, NF-I, NF-2, BCRA2, p16, FHIT, WT-I, MEN-I, MEN-II, BRCA1, VHL, FCC, MCC, ras, myc, neu, raf erb, src, fms, jun, trk, ret, gsp, hst, bcl, and abl.

In vivo and ex vivo treatments are applied using the appropriate methods worked out for the gene delivery of a particular construct for a particular subject. For example, for viral vectors, one typically delivers $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies.

An attractive feature of the present invention is that the therapeutic compositions may be delivered to local sites in a patient by a medical device. Medical devices that are suitable for use in the present invention include known devices for the localized delivery of therapeutic agents. Such devices include, but are not limited to, catheters such as injection catheters, balloon catheters, double balloon catheters, microporous balloon catheters, channel balloon catheters, infusion catheters, perfusion catheters, etc., which are, for example, coated with the therapeutic agents or through which the agents are administered; needle injection devices such as hypodermic needles and needle injection catheters; needleless injection devices such as jet injectors; coated stents, bifurcated stents, vascular grafts, stent grafts, etc.; and coated vaso-occlusive devices such as wire coils.

Exemplary devices are described in U.S. Pat. Nos. 5,935,114; 5,908,413; 5,792,105; 5,693,014; 5,674,192; 5,876,445; 5,913,894; 5,868,719; 5,851,228; 5,843,089; 5,800,519; 5,800,508; 5,800,391; 5,354,308; 5,755,722; 5,733,303; 5,866,561; 5,857,998; 5,843,003; and 5,933,145; the entire contents of which are incorporated herein by reference. Exemplary stents that are commercially available and may be used in the present application include the RADIUS (Scimed Life Systems, Inc.), the SYMPHONY (Boston Scientific Corporation), the Wallstent (Schneider Inc.), the PRECEDENT II (Boston Scientific Corporation) and the NIR (Medinol Inc.). Such devices are delivered to and/or implanted at target locations within the body by known techniques.

XI. Photodynamic Therapy

In some embodiments, the therapeutic complexes of the present invention comprise a photodynamic compound and a targeting agent that is administred to a patient. In some embodiments, the targeting agent is then allowed a period of time to bind the 'target' cell (e.g. about 1 minute to 24 hours) resulting in the formation of a target cell-target agent complex. In some embodiments, the therapeutic complexes comprising the targeting agent and photodynamic compound are then illuminated (e.g., with a red laser, incandescent lamp, X-rays, or filtered sunlight). In some embodiments, the light is aimed at the jugular vein or some other superficial blood or lymphatic vessel. In some embodiments, the singlet oxygen and free radicals diffuse from the photodynamic compound to the target cell (e.g. cancer cell or pathogen) causing its destruction.

XII. Pharmaceutical Formulations

Where clinical applications are contemplated, in some embodiments of the present invention, the nanodevices are prepared as part of a pharmaceutical composition in a form appropriate for the intended application. Generally, this entails preparing compositions that are essentially free of pyrogens, as well as other impurities that could be harmful to humans or animals. However, in some embodiments of the present invention, a straight dendrimer formulation may be administered using one or more of the routes described herein.

In preferred embodiments, the nanodevices are used in conjunction with appropriate salts and buffers to render delivery of the compositions in a stable manner to allow for uptake by target cells. Buffers also are employed when the nanodevices are introduced into a patient. Aqueous compositions comprise an effective amount of the nanodevice to cells dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. Except insofar as any conventional media or agent is incompatible with the vectors or cells of the present invention, its use in therapeutic compositions is contemplated. Supplementary active ingredients may also be incorporated into the compositions.

In some embodiments of the present invention, the active compositions include classic pharmaceutical preparations. Administration of these compositions according to the present invention is via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection.

The active nanodevices may also be administered parenterally or intraperitoneally or intratumorally. Solutions of the active compounds as free base or pharmacologically acceptable salts are prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it may be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, the dendrimer compositions are administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution is suitably buffered, if necessary, and the liquid diluent first rendered isotonic with sufficient saline or glucose. These particular aqueous solutions are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). In some embodiments of the present invention, the active particles or agents are formulated within a therapeutic mixture to comprise about 0.0001 to 1.0 milligrams, or about 0.001 to 0.1 milligrams, or about 0.1 to 1.0 or even about 10 milligrams per dose or so. Multiple doses may be administered.

Additional formulations that are suitable for other modes of administration include vaginal suppositories and pessaries. A rectal pessary or suppository may also be used. Suppositories are solid dosage forms of various weights and shapes, usually medicated, for insertion into the rectum, vagina or the urethra. After insertion, suppositories soften, melt or dissolve in the cavity fluids. In general, for suppositories, traditional binders and carriers may include, for example, polyalkylene glycols or triglycerides; such suppositories may be formed from mixtures containing the active ingredient in the range of 0.5% to 10%, preferably 1%–2%. Vaginal suppositories or pessaries are usually globular or oviform and weighing about 5 g each. Vaginal medications are available in a variety of physical forms, e.g., creams, gels or liquids, which depart from the classical concept of suppositories. In addition, suppositories may be used in connection with colon cancer. The nanodevices also may be formulated as inhalants for the treatment of lung cancer and such like.

XIII. Method Of Treatment Or Prevention Of Cancer and Pathogenic Diseases

In specific embodiments of the present invention methods and compositions are provided for the treatment of tumors in cancer therapy. It is contemplated that the present therapy can be employed in the treatment of any cancer for which a specific signature has been identified or which can be targeted. Cell proliferative disorders, or cancers, contemplated to be treatable with the methods of the present invention include human sarcomas and carcinomas, including, but not limited to, fibrosarcoma, myxosarcoma, liposarcoma, chondrosarcoma, osteogenic sarcoma, chordoma, angiosarcoma, endotheliosarcoma, lymphangiosarcoma, Ewing's tumor, lymphangioendotheliosarcoma, synovioma, mesothelioma, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilns' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrbm's macroglobulinemia, and heavy chain disease.

It is contemplated that the present therapy can be employed in the treatment of any pathogenic disease for which a specific signature has been identified or which can be targeted for a given pathogen. Examples of pathogens contemplated to be treatable with the methods of the present invention include, but are not limited to, *Legionella peomophilia, Mycobacterium tuberculosis, Clostridium tetani, Hemophilus influenzae, Neisseria gonorrhoeae, Treponema pallidum, Bacillus anthracis, Vibrio cholerae, Borrelia burgdorferi, Cornebacterium diphtheria, Staphylococcus aureus*, human papilloma virus, human immunodeficiency virus, rubella virus, polio virus, and the like.

EXAMPLES

The following examples are provided to demonstrate and further illustrate certain preferred embodiments of the present invention and are not to be construed as limiting the scope thereof.

Example 1

Quantitative MTT Biocompatibility/Cytotoxicity Assays

This Example describes quantitative MTT biocompatibility/cytotoxicity assays in both mouse and rat primary fibroblasts to measure cytotoxicity of various individual dendrimers and core-shell dendrimer molecules. In particular, the cytotoxicity of PAMAM dendrimers (G5 and G7 generations), POPAM dendrimers (generations 2, 3, and 4), and core-shell dendrimer molecules (i.e., POPAM 'core' dendrimer molecules covalently linked to 2 or 3 PAMAM 'shell' dendrimers) were analyzed employing a standard quantitative MTT assay (See Kuhlmann et al., 1998; Sladowski et al., 1993; Wang et al., 1996; Watanabe et al, 1994).

Briefly, both the mouse and rat primary fibroblasts were cultured for 24 hours with MTT (3-(4,5-dimethylthiazol-2-yi)-2 diphenyl tetrazolium bromide), and either PAMAM dendrimers, POMAM dendrimers, or the core-shell dendrimer molecules. The quantity of viable cells was then measured by absorbance at 540 nm in order to detect the formazan product (purple) resulting from the cleavage of MTT (yellow) present only in viable cells.

The results of these assays revealed a sharp distinction between the cytotoxicity of the POPAM dendrimers and both the PAPAM dendrimers and the core-shell dendrimers of the present invention. Specifically, the PAPAM dendrimers (G5 and G7 generations) assayed produced no significant in vitro cytotoxicity at concentrations up to 40 µg/ml. In contrast, the three types of POPAM dendrimers (generations 2, 3, and 4) induced concentration-related cytotoxic effects with $CL_{50}$ concentrations of 40, 12, and 12 µg/ml respectively for murine fibroblasts, and 30, 9, and 9 µg/ml respectively for rat fibroblasts. Interestingly, the core-shell dendrimer molecules did not share the cytotoxicity problems of POPAM dendrimers as only concentrations of the core-shell dendrimers higher than 30 µg/ml produced detectable toxicity, with only 5–10% of the cells killed after 24 hours exposure to 40 µg/ml. These results demonstrate the favorable biocompatability properties of the core-shell dendrimer molecules of the present invention.

Example 2

Construction of a Multifunctional Dendrimer Molecule

This example describes the construction of a multifinctional dendrimer molecule with both targeting and signaling units. In particular, this example describes the construction of a generation 5 (G5) PAMAM dendrimer conjugated to folic acid and fluorescein where remaining amino surface groups on the dendrimer are 'capped' with acetic anhydride or glycidol.

Figure 8:
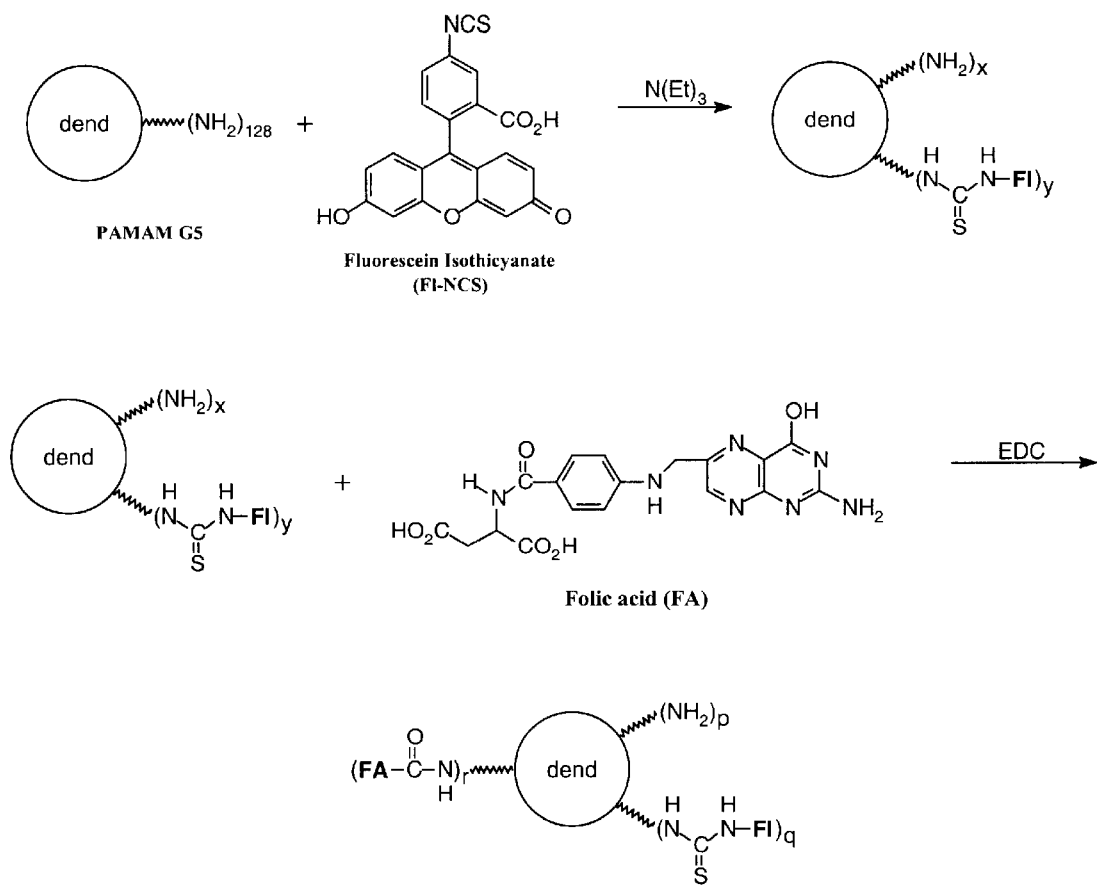
FIG. 8 shows a dendrimer synthesis procedure in some embodiments of the present invention.

The schematic for production of the dendrimers if provided in FIG. 8. Conjugation of the G5 PAMAM dendrimers was carried out by reacting G5 PAMAM G5 with fluorescein isothiocyanate and $N(Et)_3$. This fluorescein construct was then reacted with folic acid and EDC. Reaction of the remaining amino surface groups of the product with either acetic anhydride or glycidol resulted in their conversion to acetamido or bis(2,3-hydroxypropyl)amino moieties, respectively. These biologically- and charge-neutral "capping" groups gave the folate/fluorescein products and high aqueous solubility. G5 PAMAM; dendrimers were purified via ultrafiltration of pH-neutralized material in 1:1 DMSO/water.

Example 3

In Vitro Screening Assays

The toxicity and efficacy of the nanodevices of the present invention may be assayed in vitro. In preferred embodiments, the nanodevices are tested in cell culture models. For example, the efficacy of nanodevice for diagnosing, monitoring, and treating breast cancer may be assayed in breast cancer cell lines. For example, dendrimers that target breast cancer cells are generated by conjugating ligands or antibodies that specifically recognize receptors over-expressed by a particular breast cancer cell line. For example, the SUM-52 cell line has an amplification of and over-expresses the FGFR-2, c-MET, and NCAM-1 genes. The products of all of these genes are expressed to high levels on the surface of SUM-52 cells and are not expressed to appreciable levels on normal cells, or on other breast cancer cells. Libraries of dendrimers containing candidate binding partners for any of these surface exposed factors are exposed to the cells and candidate with specific and high binding affinity are identified. Similar assays may be conducted with imaging components, therapeutic components, and the like. For example, a library of dendrimers comprising different therapeutic agents are exposed to the cell line. The ability of the agent to alter cell growth or kill the cell, while not harming normal cells is screened. Ideally, such assays are conducted in multi-well plates to allow the screening of large numbers of candidates simultaneouly or in a short time period. In preferred embodiments, the screening assays are automated. For example, screening for anti-cancer compounds that induce apoptosis can be automated by providing a system for detecting the colorimetric changes induced by apoptosis (e.g., colorimetric changes caused by the imaging components of the present invention, as described above).

Any number of cell lines may be used in the screening assays. For example, for breast cancer, the cell lines SUM-190 and SUM-225 have an amplification of and overexpress HER-2. Thus, antibodies, such as the humanized version of 4D5 (herceptin), can be used to target dendrimers specifically to these cells. SUM-149, SUM-159, and SUM-229 all over-express the EGFR. Thus, EGR, TGF-α, or amphiregulin are used to target dendrimers to these cells. SUM-44 cells express HER-4 and thus are trageted using heregulin-dendrimer conjugates. A variety of human mammary cell lines available from ATCC may be used as controls including BT20, MCF7, UACC-893, and UACC812. These cells differ in the expression of HER-2 and MUC1. Screening assays may be performed in isolated cell populations and mixed cell populations.

Example 4

Killing of Drug-resistant Cells

Figure 9:
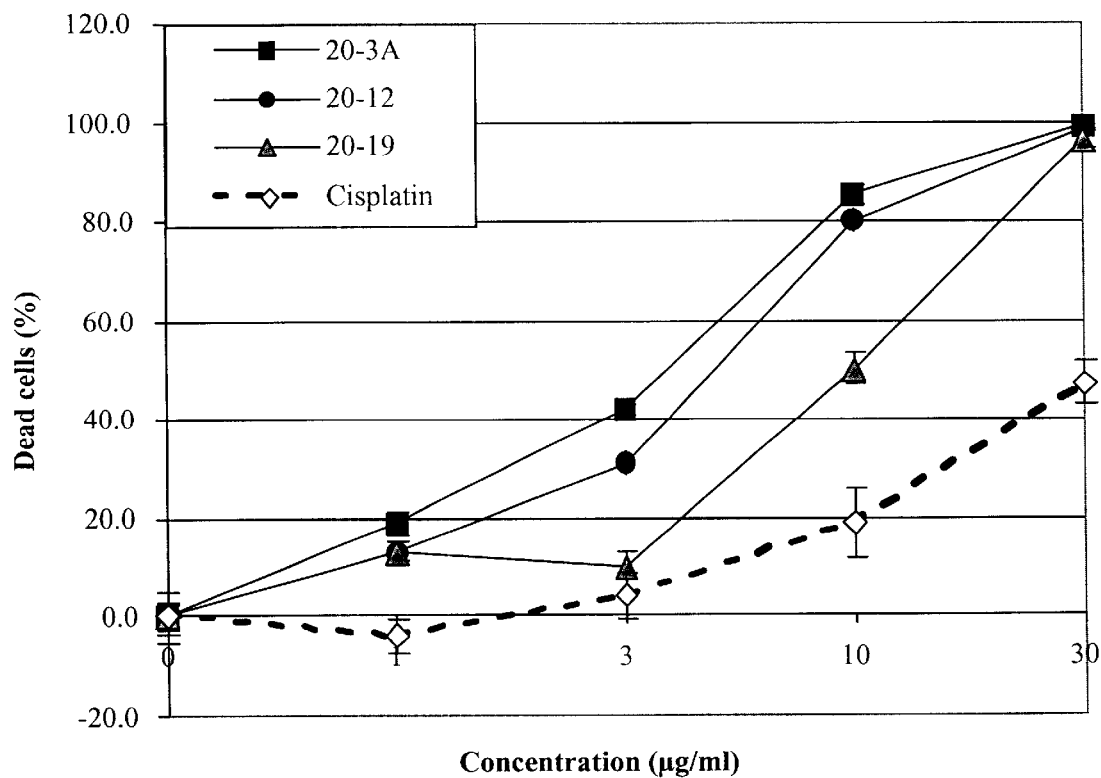
FIG. 9 shows a graph indicating the toxicity level of certain dendrimers comprising a therapeutic agent.

This example describes the killing of cisplatin resistant cell using cisplatin conjugated to dendrimers. In these experiments, cell viability was assessed using the tetrazolium-based colorimetric MTT assay (discussed in more detail below) (Mosmann, J. Immunol. Meth., 65:55 [1983]). Human cell line 16N2 was grown in serum free, Ham's F-12 medium supplemented with 5% BSA, insulin, and hydrocortisone. Cells were seeded in 96-well microtitre plates at $1 \times 10^4$/well. After 24 hours, the medium was changed and cisplatin (Stem Chemicals) or Dendrimer/Platin conjugates were added to the wells. Cell viability was evaluated after 72 hours by MTT assay. The results are shown in FIG. 9. In FIG. 9, drug concentration is expressed in platinum equivalents. Results are expressed as a percentage of the dead cells with respect to control cells grown in the absence of drug. Data represent mean+/−SEM (n=4). The Polymer 1 and Polymer 2 samples are both generation 3.5 PAMAM dendrimers conjugated with different content of platinum (E3.5-COONa:Pt with 19.25 and 20.26% of Pt, respectively). The hydrogel compound is a generation 4 PAMAM dendrimer conjugated with Pt (E4NH$_2$:Pt gel containing 6.25% Pt).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in biochemistry, immunology, chemistry, molecular biology, the medical fields or related fields are intended to be within the scope of the following claims.

What is claimed is:

1. A composition comprising a dendrimer complex, said dendrimer complex comprising covalently linked first and second dendrimers, said first dendrimer comprising a first agent and said second dendrimer comprising a second agent, wherein said first dendrimer is different from said second dendrimer, and wherein said first agent is different than said second agent.

2. The composition of claim 1, wherein said first and said second agents are selected from the group consisting of therapeutic agents, biological monitoring agests, biological imaging agents, and targeting agents.

3. The composition of claim 1, further comprising a third dendrimer, wherein said third-dendrimer is covalently linked to said first and said second dendrimers.

4. The composition of claim 3, further comprising a third agent complexed with said third dendrimer.

5. The composition of claim 3, further comprising a fourth dendrimer comprising a third agent, wherein said fourth dendrimer is covalently linked to said third dendrimer.

6. The composition of claim 5, further comprising a fifth dendrimer comprising a fourth agent, wherein said fifth dendrimer is complexed with said third dendrimer.

7. The composition of claim 1, wherein said first agent is a therapeutic agent and said second agent is a biological monitoring agent.

8. The composition of claim 7, wherein said therapeutic agent is selected from the group consisting of a chemotherapeutic agent, an anti-oncogenic agent, an anti-vascularizing agent, and an expression construct comprising a nucleic acid encoding a therapeutic protein.

9. The composition of claim 7, wherein said therapeutic agent is protected with a protecting group selected from photo-labile, radio-labile, and enzyme-labile protecting groups.

10. The composition of claim 8, wherein said chemotherapeutic agent is selected from the group consisting of platinum complex, verapamil, podophyllotoxin, carboplatin, procarbazine, mechlorethamine, cyclophosphamide, camptothecin, ifosfamide, melphalan, chlorambucil, bisulfan, nitrosurea, adriamycin, dactinomycin, daunorubicin, doxorubicin, bleomycin, plicomycin, mitomycin, etoposide, tamoxifen, taxol, transplatinum, 5-fluorouracil, vincristin, vinblastin, and methotrexate.

11. The composition of claim 8, wherein said anti-oncogeric agent comprises an antisense nucleic acid.

12. The composition of claim 11, wherein said antisense nucleic acid comprises a sequence complementary to an RNA of an oncogene.

13. The composition of claim 12, wherein said oncogene is selected from the group consisting of abl, Bcl-2, Bcl-$x_1$, erb, fms, gsp, hst, jun, myc, neu, raf, ras, ret, src, and trk.

14. The composition of claim 8, wherein said nucleic acid encodes a factor selected from the group consisting of tumor suppressors, cytokines, receptors, inducers of apoptosis, and differentiating agents.

15. The composition of claim 14, wherein said tumor suppressor is selected from the group consisting of BRCA1, BRCA2, C-CAM, p16, p21, p53, p73, Rb, and p27.

16. The composition of claim 14, wherein said cytokine is selected fr om the group consisting of GMCSF, IL-1, IL-2, IL-3, IL-4, IL-5, IL-6, IL-7, IL-8, IL-9, IL-10, IL-11, IL-12, IL-13, IL-14, IL-15, β-inteferon, γ-interferon, and TNF.

17. The composition of claim 14, wherein said receptor is selected from the group consisting of CFTR, EGFR, estrogen receptor, IL-2 receptor, and VEGFR.

18. The composition of claim 14, wherein said inducer of apoptosis is selected from the group consisting of AdE1B, Bad, Bak, Bax, Bid, Bik, Bim, Harakid, and ICE-CED3 protease.

19. The composition of claim 2, wherein said biological monitoring agent comprises an agent that measures an effect of a therapeutic agent.

20. The composition of claim 2, wherein said therapeutic agent comprises a short-half life radioisotope.

21. The composition of claim 21, wherein said biological imaging agent comprises a radioactive label selected from the group consisting of $^{14}$C, $^{36}$Cl, $^{57}$Co, $^{58}$Co, $^{51}$Cr, $^{125}$I, $^{131}$I, $^{111}$In, $^{152}$Eu, $^{59}$Fe, $^{67}$Ga, $^{32}$P, $^{186}$Re, $^{35}$S, $^{75}$Se, Tc-99m, and $^{175}$Yb.

22. The composition of claim 19, wherein said monitoring agent is capable of measuring the amount of apoptosis caused by said therapeutic agent.

23. The composition of claim 2, wherein said targeting agent is selected from the group consisting of antibody, receptor ligand, hormone, vitamin, and antigen.

24. The composition of claim 23, wherein said antibody is specific for a disease specific antigen.

25. The composition of claim 24, wherein said disease specific antigen comprises a tumor specific antigen.

26. The composition of claim 23, wherein said receptor ligand is selected from the group consisting of a ligand for CFTR, FGFR, estrogen receptor, FGR2, folate receptor, IL-2 receptor, glycoprotein, and VEGPR.

27. The composition of claim 3, wherein said first and second dendrimers comprise PAMAM dendrimers and wherein said third dendrimer comprises a POPAM dendriiner.

28. A method of treating a cell comprising:
a) providing:
   i) an in vitro or ex vivo cell; and
   ii) a composition comprising a dendrimer complex, said dendrimer complex comprising covalently linked first and second dendrimers, said first dendrimer comprising a first agent and said second dendrimer comprising a second agent, wherein said first dendrimer is different from said second dendrimer, and wherein said first agent is different than said second agent; and
b) exposing said cell to said composition.

29. The method of claim 28, wherein said first and said second agents are selected from the group consisting of therapeutic agents, biological monitoring agents, biological imaging agents, and targeting agents.

30. The method of claim 28, further comprising a third dendrimer, wherein said third-dendrimer is covalently linked to said first and said second dendrimers.

31. The method of claim 30, further comprising a third agent complexed with said third dendrimer.

32. The method of claim 30, further comprising a fourth dendrimer comprising a third agent, wherein said fourth dendrimer is covalently linked to said third dendrimer.

33. The method of claim 32, further comprising a fifth dendrimer comprising a fourth agent, wherein said fifth dendrimer is complexed with said third dendrimer.

34. The method of claim 28, wherein said first agent is a therapeutic agent and said second agent is a biological monitoring agent.

* * * * *